United States Patent
Carmeli et al.

(10) Patent No.: US 9,014,786 B2
(45) Date of Patent: Apr. 21, 2015

(54) DEVICE AND METHOD FOR OPENING VASCULAR OBSTRUCTIONS

(75) Inventors: Ran Carmeli, Rinatya (IL); Jonathan Einav, Raanana (IL); Itai Yonat, Tel-Aviv (IL)

(73) Assignee: Eyoca Medical Ltd., Tel-Aviv (IL)

( * ) Notice: Subject to any disclaimer, the term of this patent is extended or adjusted under 35 U.S.C. 154(b) by 385 days.

(21) Appl. No.: 13/492,098

(22) Filed: Jun. 8, 2012

(65) Prior Publication Data

US 2012/0302820 A1 Nov. 29, 2012

Related U.S. Application Data

(63) Continuation-in-part of application No. 11/914,095, filed on Jul. 8, 2008, now Pat. No. 8,295,908, and a continuation-in-part of application No. 12/516,431, filed on Mar. 10, 2010, now abandoned.

(51) Int. Cl.

| | |
|---|---|
| *A61B 5/055* | (2006.01) |
| *A61B 5/053* | (2006.01) |
| *A61B 17/00* | (2006.01) |
| *A61B 17/22* | (2006.01) |
| *A61M 25/00* | (2006.01) |
| *A61B 8/08* | (2006.01) |
| *A61B 8/12* | (2006.01) |
| *A61M 25/01* | (2006.01) |
| *A61M 25/09* | (2006.01) |

(52) U.S. Cl.
CPC ..... *A61B 5/0538* (2013.01); *A61B 2017/00026* (2013.01); *A61B 2017/22008* (2013.01); *A61B 2017/22014* (2013.01); *A61B 2017/22042* (2013.01); *A61M 25/00* (2013.01); *A61B 8/0891* (2013.01); *A61B 8/12* (2013.01); *A61M 25/01* (2013.01); *A61M 25/09* (2013.01)

(58) Field of Classification Search
USPC .............. 600/407, 410, 423; 601/2–4; 604/22
See application file for complete search history.

(56) References Cited

U.S. PATENT DOCUMENTS

| 3,570,476 A | 3/1971 | Gregg |
|---|---|---|
| 4,688,569 A | 8/1987 | Rabinowitz |

(Continued)

FOREIGN PATENT DOCUMENTS

| DE | 4215901 | 8/1993 |
|---|---|---|
| DE | 10223371 | 8/2003 |

(Continued)

*Primary Examiner* — Peter Luong
(74) *Attorney, Agent, or Firm* — Tarolli, Sundheim, Covell & Tummino LLP

(57) ABSTRACT

The present invention is directed to a device and method for opening obstructed body internal passages and for sensing and characterizing tissues and substances in contact with the device. In general, the device comprises a catheter tube capable of inducing vibrations in a guidewire contained therein, wherein said vibrations of the guidewire are utilized for opening a passage through an occlusion. The in-vivo vibrations may be induced by means of a magnetic field actuating means and a guidewire comprising magnetic coupling means, or by means of transducers, which may be also used for the sensing. The invention also relates to the field of minimal invasive catheterization, particularly an apparatus for opening and/or removing obstructions occluding body internal passages by means of an active guidewire comprising a coil to which an alternating voltage can be applied. In that way the guidewire can vibrate if an external magnetic field is applied.

15 Claims, 14 Drawing Sheets

(56) References Cited

U.S. PATENT DOCUMENTS

| | | |
|---|---|---|
| 5,234,451 A | 8/1993 | Osypka |
| 5,372,144 A | 12/1994 | Mortier et al. |
| 5,569,179 A | 10/1996 | Adrian |
| 5,628,719 A | 5/1997 | Hastings et al. |
| 5,813,996 A | 9/1998 | St. Germain et al. |
| 6,673,064 B1 | 1/2004 | Rentrop |
| 6,685,643 B1 | 2/2004 | Waldinger et al. |
| 6,685,644 B2 | 2/2004 | Seo et al. |
| 6,702,748 B1 | 3/2004 | Nita et al. |
| 6,800,085 B2 | 10/2004 | Selmon et al. |
| 6,852,109 B2 | 2/2005 | Winston et al. |
| 2005/0216044 A1 | 9/2005 | Hong |
| 2009/0209900 A1 | 8/2009 | Carmeli et al. |

FOREIGN PATENT DOCUMENTS

| | | |
|---|---|---|
| EP | 0934727 | 8/1999 |
| WO | 9412234 | 6/1994 |
| WO | 9608196 A1 | 3/1996 |
| WO | 0000252 | 1/2000 |
| WO | 2006120674 | 11/2006 |

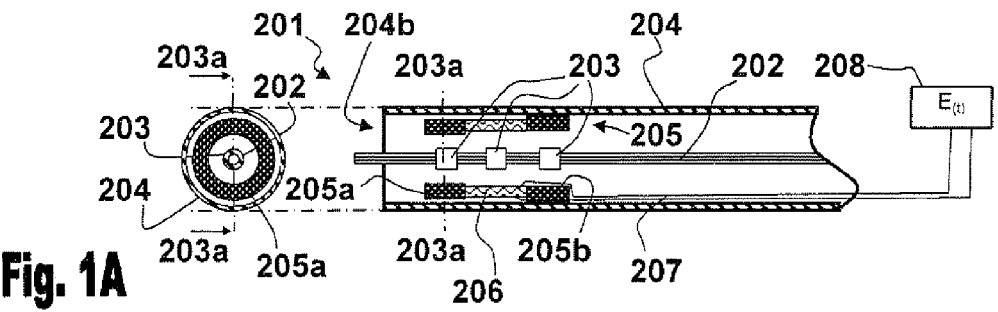
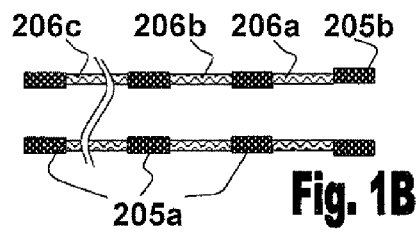
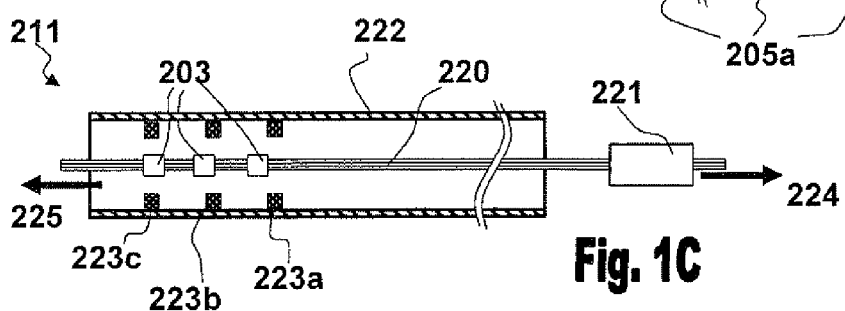
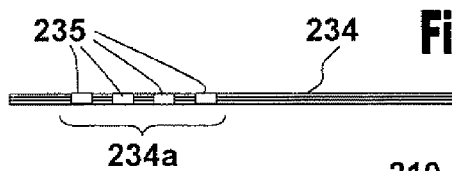
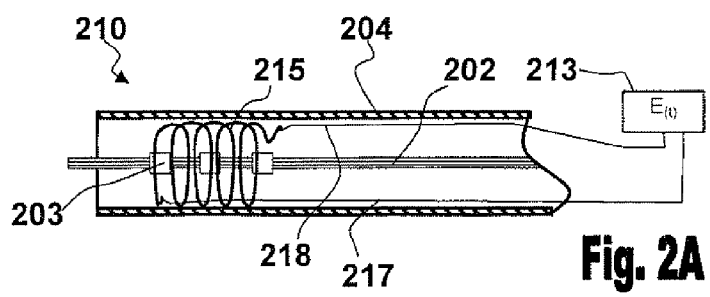
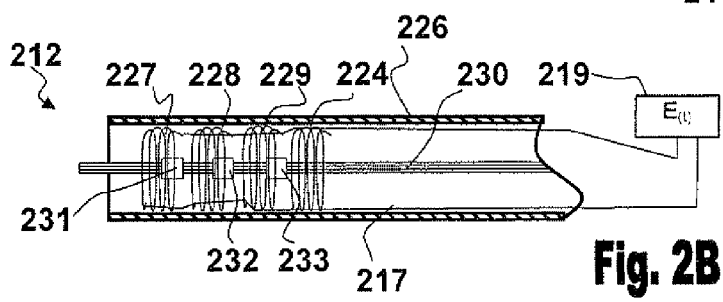

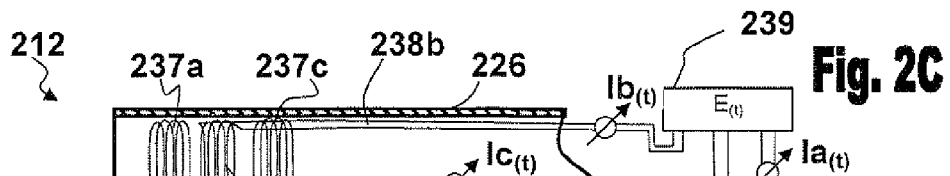
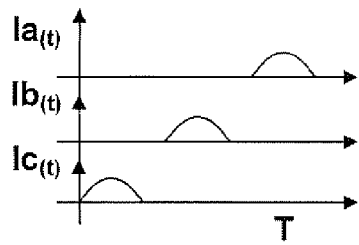
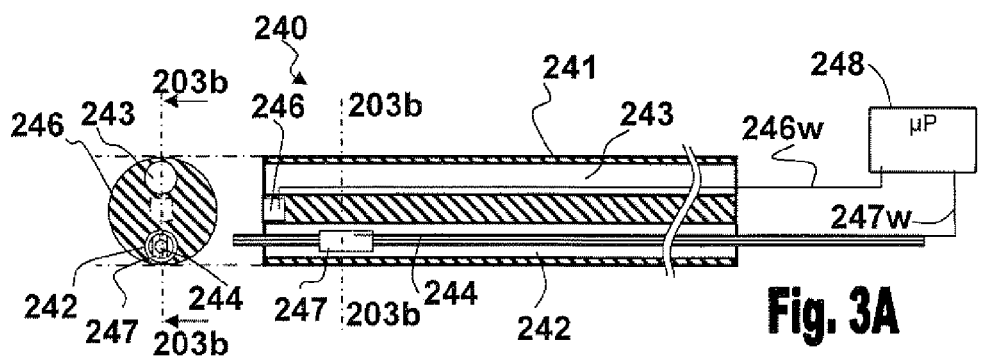
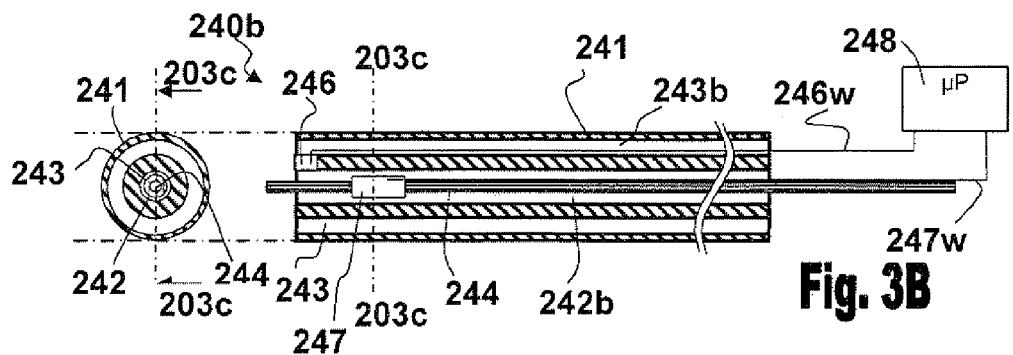

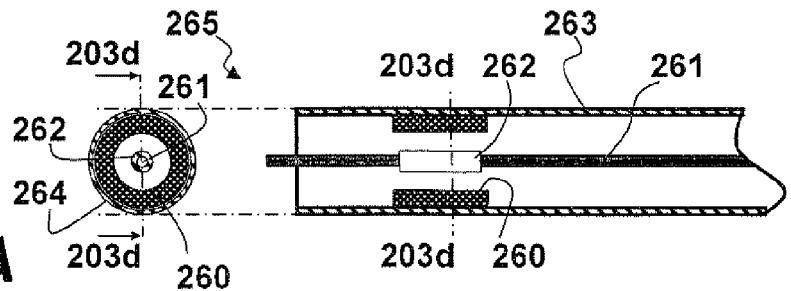
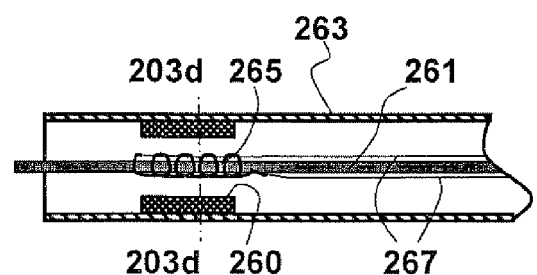
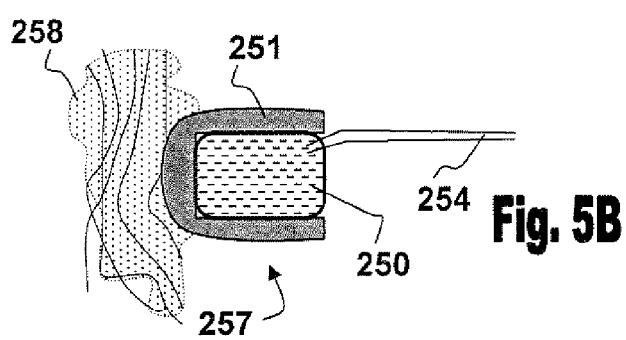
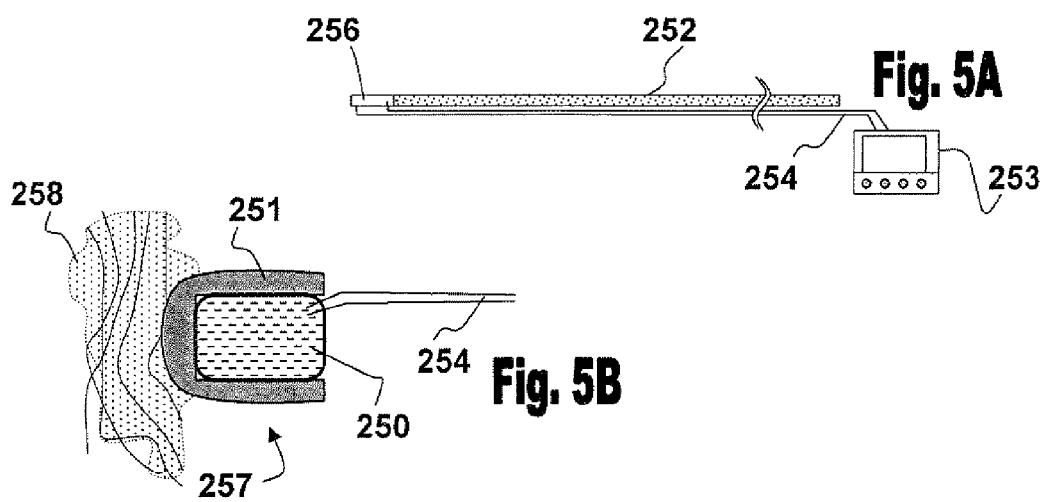
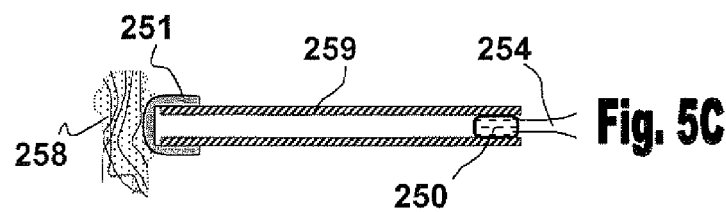

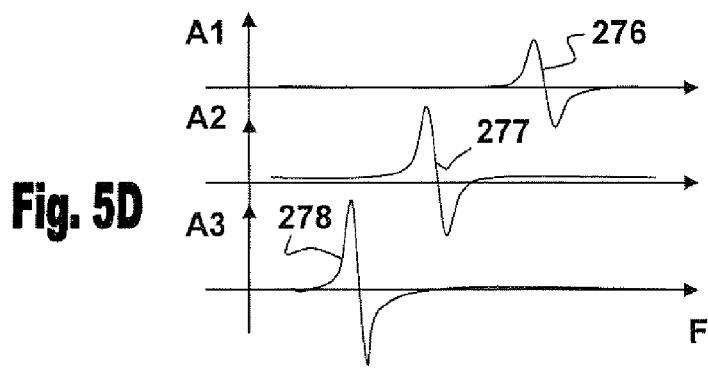
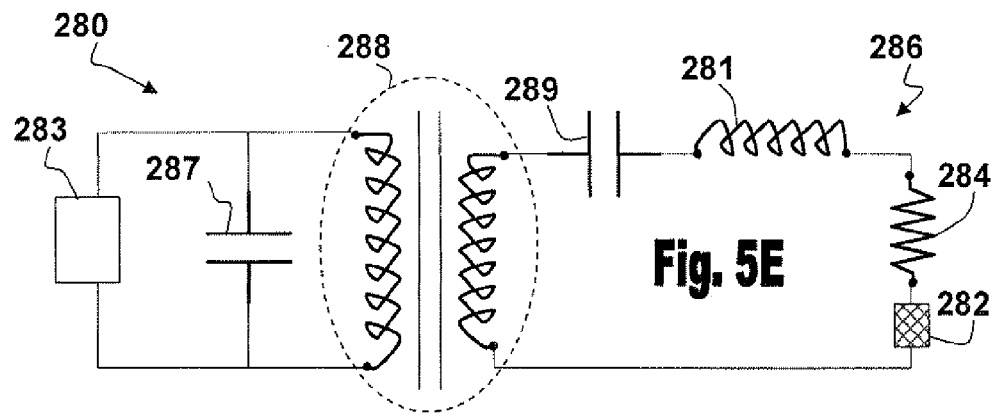
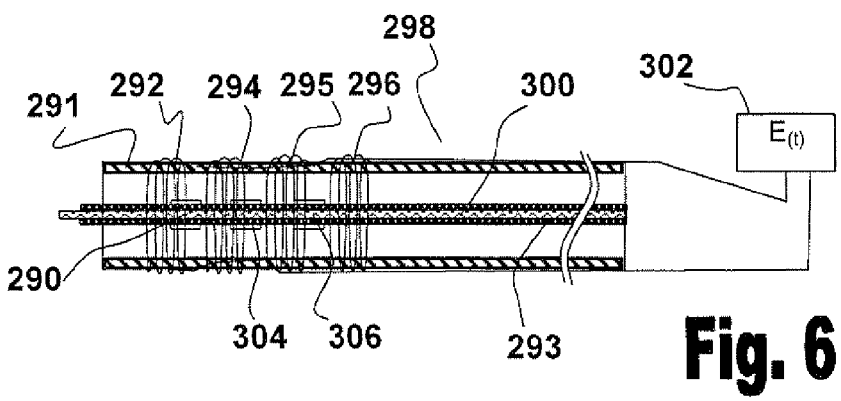

PRIOR ART

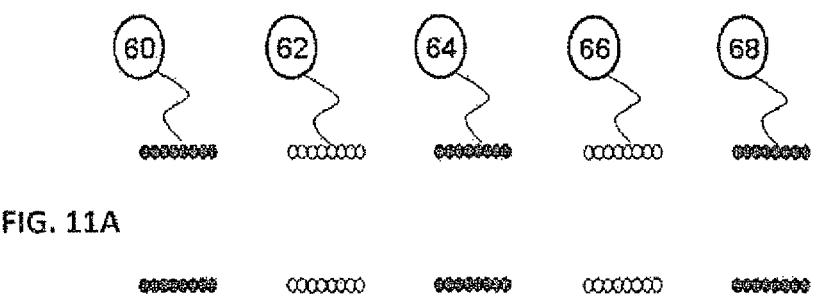
FIG. 11A
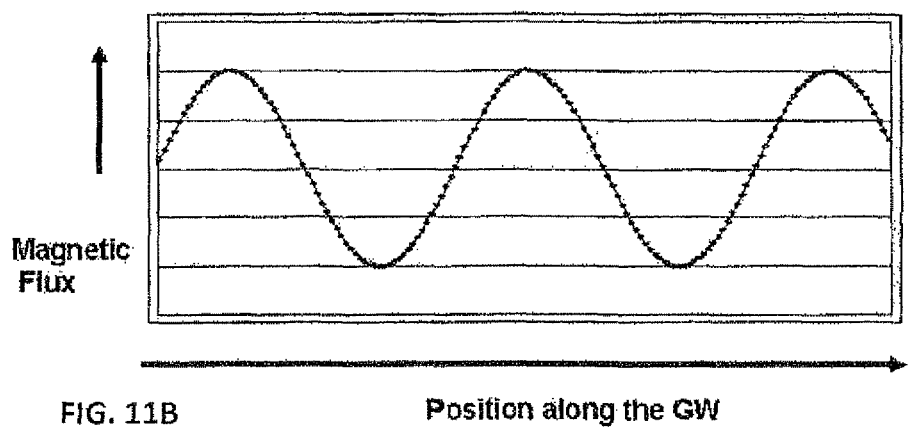
FIG. 11B   Position along the GW

South pole　　North pole

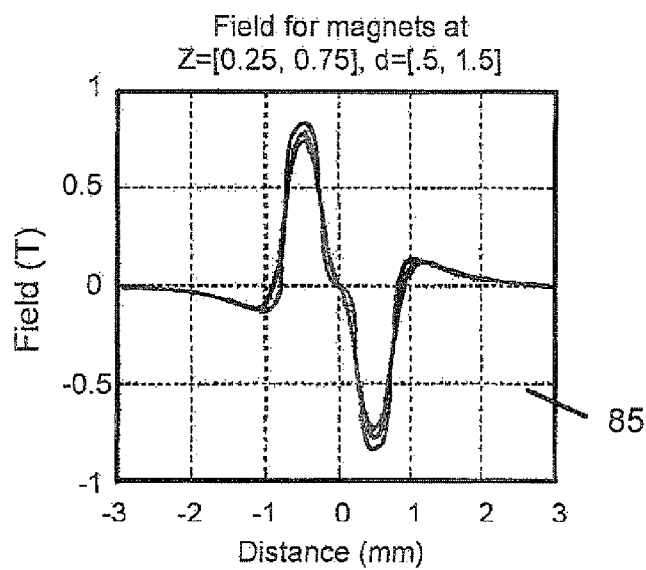
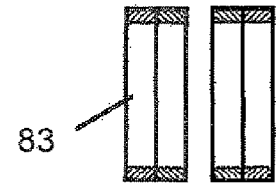
Fig. 13C
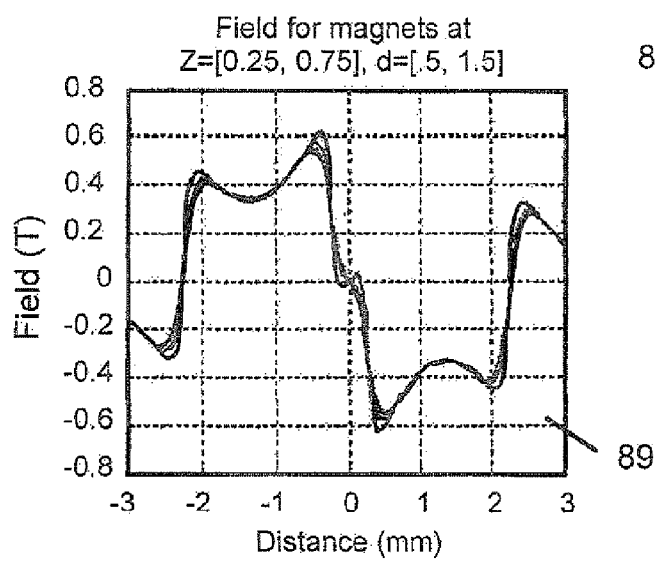
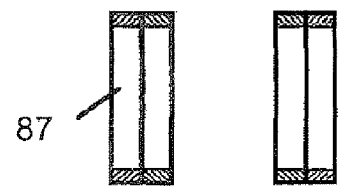
Fig. 13D

DEVICE AND METHOD FOR OPENING VASCULAR OBSTRUCTIONS

RELATED APPLICATIONS

This Application is a CIP of U.S. patent application Ser. No. 11/914,095, filed Jul. 8, 2008 now U.S. Pat. No. 8,295,908, which claims the benefit of PCT/IL2006/000541, filed May 9, 2006, which claims the benefit of IL 168568, filed May 11, 2005, IL 168569, filed May 11, 2005, and IL 170412, filed Aug. 22, 2005. This application is also a CLP of U.S. patent application Ser. No. 12/516,431, filed Mar. 10, 2010 now abandoned, which claims the benefit of PCT/IL2007/001435, filed Nov. 21, 2007, which claims the benefit of IL 179618, filed Nov. 27, 2006.

FIELD OF THE INVENTION

The present invention relates to the field of minimal invasive catheterization. More particularly, the invention relates to a method and apparatus for opening and/or removing obstructions occluding body internal passages and for in vivo sensing of substance/tissue in body internal passages and body organs.

In particular, the invention relates to an apparatus for opening and/or removing obstructions occluding body internal passages by means of an active guidewire. More particularly, the invention relates to an active oscillating guidewire, capable of passing through an occluded vessel.

BACKGROUND OF THE INVENTION

Many vasocclusive events, such as heart attacks and strokes, are caused by plaque build-ups in arteries. As one specific example, atherosclerotic plaque is known to build-up in the walls of arteries in the human body. Such plaque build-up restricts circulation and often causes cardiovascular problems, especially when the build-up occurs in coronary arteries.

One common method for opening partially occluded body internal passages is to guide a medical device to the diseased site, where it is used to carry out the needed treatment. A guidewire is usually used for advancing a catheter device thereover via body internal passages towards the treatment site. Typically, the distal tip of the guidewire is introduced into the body of the treated subject via an incision and advanced therethrough towards the treatment site, thereby forming a path leading to the occluded site through said body internal passages. The catheter, or any other suitable treatment devices (e.g., balloon catheter, stent or rotational atherectomy device), may be then threaded over the guidewire and advanced through said internal passages using the guidewire as a rail.

Total or near-total occlusions in body internal passages can, partially or entirely, block the passage therethrough. For example, in patients who suffer from coronary CTO (chronic total occlusion), the successful performance of a Percutaneous Transluminal Coronary Angioplasty (PTCA) is a technical challenge. The factor that is most determinative of whether the practitioner can successfully perform PTCA on patients suffering from coronary CTO is his ability (or inability) to advance a suitable guidewire from a position proximal of the lesion to a position distal of the lesion while remaining inside the true vessel lumen (without performing perforation or dissection of the artery wall).

In some instances, such as where the occlusive matter is soft or where the body internal passage is partially occluded, the guidewire can easily be pushed through the occlusive matter itself, thereby allowing the guidewire to remain within the body internal passage. However, in other cases, such as when the body internal passage is totally occluded by hard plaque (e.g., calcified atherosclerotic plaque), the guidewire cannot cross the occlusion and may deviate to the side and penetrate through layers of the passage walls (e.g., the intima—inner layer of a vessel wall), thereby creating a neo-lumen therethrough (e.g., through the sub-intimal space—within the wall of the artery between the intima and media, or adventitia, i.e. a dissection), or even completely exit said internal passage, i.e. a perforation.

Several techniques are known for passing through an occluded internal passage, such as laser catheters (U.S. Pat. No. 6,673,064), ultra sonic catheters (U.S. Pat. No. 6,702,748), and tissue displacement or hinged expansion devices (U.S. Pat. No. 6,800,085). In all of those techniques the occlusion is opened by means of a catheter device equipped with operative means for occlusions opening. However, the prior art devices suffer from lack of flexibility and maneuverability due to the bulky structure of their catheter devices. Consequently, the treatment procedures which utilize these prior art devices are substantially different from conventional catheterization procedure workflow as commonly practiced in regular cases (non CTO cases).

The aforementioned prior art solutions also suffer from lack of ability to indicate to the practitioner in real time, i.e. while carrying out the procedure, whether he is navigating the treatment devices through the occlusion (true lumen) or if he is actually perforating or dissecting the body internal passage, e.g. the artery.

Other known procedures, such as described in U.S. Pat. No. 6,852,109, propose a method for forming a passage through the CTO by a guidewire having active Radio Frequency (RF) ablation tip, with Optical Coherence Reflectometry (OCR) capability for sensing the position of the tip. However this known type of guidewire is a special guidewire comprising a mechanism for transferring RF energy and a following catheter with fiber optics for the OCR capability. These restraints are relatively rigid and therefore diminish the flexibility of the device, which is an important feature for carrying out in vivo navigation. Thus, also this prior art device suffers from lack of flexibility, and the need to deviate from the conventional practice workflow of the practitioner.

Another solution used for determining whether an organic tissue is healthy or not is using IVUS (intravascular ultrasound), for example as described in U.S. Pat. Nos. 6,685,644 and 6,685,643, however lack of data due to poor transmission in this known method and calcified build-ups that cause "acoustic shadowing" yield poor results in determining tissue type and true lumen detection.

In still another solution used such as described in U.S. Pat. No. 5,908,395, a hand held vibrator is attached to the proximal side of a guide wire, or a catheter through which the guidewire is threaded.

The guidewire then conveys the proximal vibrations to its distal end, subject to the specific passage of the guidewire through the arteries. If indeed these vibrations reach the distal end of the guidewire they may be efficient in penetrating and recanalization of CTOs (chronical total occlusions). However, there is a problem in that the vibrations may be absorbed before reaching the distal end. In addition, using an external hand held vibrator interferes with the standard operation of the guidewire, and limits the operator from conveniently controlling the guidewire by manually holding its proximal end, again causing the need to deviate from the conventional practice workflow of the practitioner.

There thus exists a need for devices and techniques for treating occluded body internal passages, for characterizing the tissue/substance the treatment device is in contact with and determining its location within and about the body internal passage, and for safely opening occlusions therein without damaging the occluded internal passage.

It is therefore an object of the present invention to provide a method and device for opening occluded body internal passages and/or body organs.

It is another object of the present invention to provide a method and device for safely navigating treatment means, such as a catheter device, to a treatment site through body internal passages.

It is a further object of the present invention to provide a method and device for in vivo characterizing the tissue and/or substance being in contact with a treatment device.

It is yet another object of the present invention to provide a catheter device capable of inducing vibrations in a guidewire contained therein.

In still another solution used as described in copending application PCT/IL2006/000541, a device comprises a magnetic guidewire housed in a coiled catheter. The guidewire is vibrated by feeding electrical current via the coils of the catheter, thus providing magnetic excitation of the guidewire tip. However, because of the magnetic guidewire structure and dimensions this solution may not be optimized to match the physician procedure. The magnets beads added to the guidewire may increase the diameter thereof, and may thus prevent the use of some devices that are threaded onto regular guidewires.

More particularly, these over-the-wire devices sometimes have a lumen that is only marginally larger in diameter than the diameter of the guidewire. By adding magnets to the guidewire, these over-the-wire devices may not suited to be threaded onto the magnetic guidewire, as the diameter of the magnets may be bigger than the inner diameter of the lumen of the catheter.

In still another solution used such as described in WO 00100252, a catheter or guidewire that is made from ferromagnetic means and is positioned such that a predetermined portion of the device lies adjacent to the target site. A magnetic field source that changes over time in magnitude and/or direction, of sufficient strength is disposed outside the patient's body in sufficient proximity to the intrabody device to induce motion in the device through the oscillating magnetic field that it emits. However this method significantly deviates from the physician regular workflow and requires the change of the catheterization lab in order to facilitate the magnet field exterior device, furthermore, it is almost impossible to guarantee that the magnetic member that lies within the body cavity will be exactly adjusted to the magnetic source.

In still another solution such as described in WO 94/12234, a flexible elongate device having a distal extremity with a vibratory impact tip embedded with a coil spring piston like mechanism for catheters and guide wires. However, because of the fact the guidewire or catheter are embedded with a spring coil vibrational mechanism, the mechanical properties of the guidewire and the catheter significantly change and the ability to pass over the wire devices is reduced, thus deviating from the standard workflow of the procedure.

Several uses of magnetic coupling of guidewires are known, such as in U.S. Pat. No. 5,813,996, however this known coupling is static and is used as a guide wire extension system including a guide wire and an extension wire and means for magnetically coupling the guide wire to the extension wire, and not as a means for magnetic vibration for gateway passage opening.

There thus exists a need for devices and techniques for treating occluded body internal passages, for characterizing the tissue/substance the treatment device is in contact with, for determining its location within and about the body internal passage, and for safely opening occlusions therein without damaging the occluded internal passage, while keeping the same work flow (clinical procedure), and enabling the physician to use exactly the same over-the-wire devices.

Further more, guidewires are a great technical and clinical challenge. The structure of the guidewire, and generally speaking composition of materials and dimensions of the different segments of the guidewire set the guidewire's characteristics. More specifically, most guidewires are constructed such that their distal portions (typically the distal 100-300 mm of the guidewire) are made of a specially shaped and tapered core, wrapped with a special spring-like coil. This coil, together with the inner shaped core of the guidewire influences dramatically the behavior and characteristics of the guidewire.

Therefore, it is desirable to be able to make use of the existing structure of conventional guidewires, and thus maintaining the critical mechanical characteristics of the guidewire, while adding the capability to generate an alternating magnetic field.

This alternating magnetic field can then serve to generate alternating magnetic forces that oscillate the tip of the guidewire providing it with active drilling capabilities to open occlusions.

It is an object of the present invention to provide a method and device for opening occluded body internal passages and or body organs, by providing additional means and implementing the coils already embedded into a guidewire in such a way so as to enable electrical generation of alternating magnetic fields.

Other objects and advantages of the invention will become apparent as the description proceeds.

SUMMARY OF THE INVENTION

The present invention is directed to a device and method for opening obstructed body internal passages and for sensing and characterizing tissues and substances being in contact with the device of the invention. In general, the device of the present invention comprises a catheter tube capable of inducing vibrations in a guidewire contained therein, wherein said vibrations of the guidewire are utilized for opening a passage through an occlusion.

More particularly, the present invention relates to a device and method for in vivo drilling in living tissue and/or finding the weak path in said living tissue, in body internal passages and body organs, which may be utilized for opening a passage suitable for passing a treatment device (e.g., a stent, balloon) through an occluded body internal passage (e.g., blood vessel), such as in cases of total occlusion (Chronic Total Occlusion—CTO). The in vivo drilling is performed by means of a unique drilling guidewire, which aside from drilling through the occlusion can enable the operator to sense the tissue/substance being in contact with the drilling part of said drilling guidewire. The sensing of the tissue/substance contacting the drilling guidewire may be advantageously used to provide an indication as to whether the drilling guidewire properly operates in the occluded internal passage or whether it deviates therefrom and injures the passage wall. The path drilled and/or opened and/or re-canalized through the occluding matter enables the passage of a conventional guidewire through the occluded passage and thereby allows carrying out the conventional treatments applicable in such cases, such as, for example, by means of balloon catheters and stents.

The drilling according to this invention is carried out by means of rapid vibrations e.g., at a frequency of about several dozens of Hz, preferably in the region of 1-200 Hz, low amplitude vibrations e.g., with an amplitude of about a fraction of a mm, preferably in the region of 0.1 to 1 mm, that are directed in vivo to the occluding matter. The in vivo drilling device of the invention is designed to transfer the drilling energy with high efficiency into hard/calcified tissue, while keeping the efficiency low, when drilling into relatively soft elastic tissues. The drilling vibrations are preferably limited to low amplitudes, resulting in a drilling scheme that transfers energy very efficiently into hard/calcified occlusions. At the same time, such drilling cannot transfer energy efficiently into soft elastic tissues, such as the artery wall, thus lowering the risk of perforation or dissection thereof.

The in vivo drilling device of the present invention is preferably implemented by a guidewire comprising magnetic coupling means adapted for inducing axial vibrations therein by means of an alternating magnetic field. The magnetic coupling means may be implemented by a number of miniature magnetic elements (e.g., having a ring shape) radially attached to a section of a conventional guidewire or embedded within some segments of the guidewire itself. By applying rapid alternating/changing magnetic fields around the guidewire section that comprises said miniature magnets rapidly vibrate that guidewire section.

The alternating/changing magnetic field may be induced by alternating the frequency and magnitude (amplitude and direction) of the magnetic field. The magnetic field may be applied in vivo by a catheter device comprising a magnetic field actuating means mounted in section thereof corresponding to the location of the magnetic coupling means on the drilling guidewire. For example, the alternating magnetic field may be applied by a coil wound on (or in) a section of a catheter device (or embedded therein) containing the drilling guidewire. An alternating magnetic field may be electrically applied by connecting the coil to an alternating electrical current source, which in effect vibrates the guidewire.

Additionally or alternatively, the alternating magnetic field is applied by vibratable fixed magnets mounted in a section of a catheter device comprising the drilling guidewire, and in a location corresponding to the location of the coupling magnets on the drilling guidewire or embedded in it. In particular, these vibratable fixed magnets can be attached to the catheter and have the shape of hollow cylinders, through which the guidewire passes. The vibration of the vibratable fixed magnets attached to the catheter may be achieved by means of electrically vibratable means, such as piezoelectric elements, which are attached to the magnets, wherein said electrically vibratable means can be powered by an external electrical power source. The power source may be of many forms, but preferably has a sinusoidal shaped output with alternating amplitude and frequency, thus providing vibrations of different characteristics.

The frequency of the vibrations may be changed in close loop in order to manually or automatically reach the resonance frequency or anti-resonance of the whole apparatus, thus gaining continuous leveling of the drilling energy.

The catheter device may include several separated electromagnet coils. Each of those coils may be independently powered by an electrical current. Thus, by applying exciting current to each coil successively, (e.g., in a "wave" manner)—it is possible to achieve a relatively constant power over long range along the catheter/guidewire (e.g., as in linear stepping motor).

The electrical power (current and voltage vs. frequency) fed into the vibrating elements, can be analyzed to measure the overall apparatus magnetic impedance, and thereby provide an indication about the type of tissue/substance drilled, as described in Israel patent application No. 168569.

In addition, by continuously measuring the coil ohmic resistance (the instant ratio between the voltage develops on the coil and the current fed through the coil, one can deduct the ambient temperature surrounding the coils. This is based on the physical characteristic of the coil material, where its resistance depends on its temperature. This continuous measurement of the temperature, may also be used for providing an alert to the practitioner and/or for performing an automatic shut off of the active vibrations, whenever too high temperature is reached, and thereafter resuming the vibrations, when the ambient temperature surrounding the coils falls down to a safe level.

Alternatively or additionally, the vibration of the drilling guidewire may be achieved by other means, such as by providing a constant distally directed force on magnetic coupling means mounted on a distal end section of the drilling guidewire, and concurrently applying alternating proximally directed force, by externally (manually or mechanically) pulling the guidewire. In this way a longitudinal and possibly also a transverse vibrating mechanism is achieved.

Alternatively or additionally, the vibrations of the drilling guidewire may be achieved by clamping the guidewire within a catheter, while vibrating said catheter. More specifically, it may be excited, by using a catheter comprising at least two conduits, e.g., an inner conduit disposed within an outer conduit. The inner conduit, such as in a balloon catheter accurately matches the guidewire diameter. Magnets, preferably miniature in size and radial in shape are attached to the wall of the inner conduit, or are embedded therein. The outer conduit of the catheter is enwrapped or embedded in a coil, preferably several coils. The inner conduit is relatively free within the outer conduit, and hence by feeding an alternating current through the coils, an alternating magnetic force develops, vibrating the inner conduit of the catheter, and hence vibrating the guidewire clamped within the lumen of said inner conduit. Alternatively, the catheter device may be operated without the guidewire by using the distal end of the inner conduit as a drilling head.

Additionally or alternatively the inner magnets may be arranged non-radially, such that the generated vibrations may progress both, in longitudinal as well as in transverse directions.

Alternatively or additionally, the distal drilling tip of the guidewire is provided with bending piezo actuators, such that, by controlling the electrical current fed into the actuator, the guidewire tip can be vibrated and/or directed into a desired direction in vivo.

The present invention also provides means for in vivo sensing the tissue/substance with which the device of the invention is in contact or in proximity with by means of one or more acoustic transducers (e.g., Piezo electric transducers) and/or provides means for analyzing the magnetic impedance of one or more electric coils that are fed by an electrical alternating current. These transducers and or coils are held in proximity to living tissues affecting the acoustic and or magnetic impedance of the volume in the vicinity of the transducers and or coils. Changes in the acoustic and/or magnetic impedance results in changes in the voltage and current vs. frequency driving the transducers and/or coils. These changes can be measured by the driver of the transducers and/or coils, that may be remotely positioned away from the transducers and/or coils themselves, i.e. outside the body.

In one preferred embodiment of the invention the device is equipped with miniature magnets mounted and/or embedded near the distal tip of a guidewire. These magnets are activated when said guidewire is threaded through electrical coils fed with an electrical current. This guidewire, when threaded into body passageways or organs, can "feel" the different magnetic impedance surrounding its tip, as the guidewire is passed through said passageways and/or organ by the practitioner. In this embodiment, the driving unit of the coils is located remotely from the coils themselves.

The magnetic impedance of the coils is preferably measured at the driving unit end (proximal end) of the catheter. This measurement may be carried out by continuously measuring the electrical voltage over the coils and dividing the same by the value of the electrical current driving said coils. The magnetic impedance may be measured at different frequencies, thus providing a more comprehensive result of magnetic impedance at different frequencies. For this purpose the driving unit may be equipped with analog to digital converters and a processing unit for converting the values of the measured electrical voltage and driving current and computing the magnetic impedance by dividing the digital representation of the measured electrical voltage by the digital representation of the driving current.

The measured impedances may be used to characterize the tissue/substance that is in contact with, or in proximity to, the guidewire distal tip and thereby to provide clinical indications (e.g., to distinguish between plaque, blood, vessel walls or any other tissue that may be in the proximity of the tip of the guidewire), thus making it possible for the practitioner to distinguish between the plaque build-up inside the artery and the vessel walls (intima, media or adventitia).

In another embodiment of the invention the device of the invention is equipped with miniature acoustic transducers mounted at the distal tip of a guidewire. This guidewire, when threaded into body passageways, can "feel" the different acoustical impedance surrounding the transducers, as the guidewire is passed through the said passageways by the practitioner. In this embodiment, the driving unit of the transducers is located distantly from the transducers themselves. The acoustic impedance is preferably measured at the driving unit end (proximal end) of the guidewire. The measured impedances may be used to characterize the tissue/substance being in contact with the guidewire distal tip and thereby to provide clinical indications (e.g., allow to distinguish between plaque, blood, vessel walls or any other tissue that may be in the proximity of the tip of the guidewire), thus making it possible for the practitioner to distinguish between the plaque build-up inside the artery and the vessel walls (media).

Additionally or alternatively, the device of the invention includes electrically vibratable means, such as an ultrasound transducer, embedded in the distal end of the drilling guidewire and/or in the catheter distal end, thereby allowing vibrating the distal end of the device at an ultrasonic frequency (controlled and regulated from a control unit connected to the proximal end of the unit in vitro) for drilling through the occlusion. The electrically vibratable means preferably comprises a micro piezoelectric device capable of efficiently transferring energy to hard/calcified tissues and thus allows destruction of plaque rather than of the elastic passageway wall.

The drilling effect of the device of the present invention is achieved by two main mechanisms: i) the direct rapid mechanical vibrations applied into the occlusion, or ii) by cavitation effect, in which the ultrasonic waves in the blood produce tiny bubbles, forming a fractal structure and radiating sound by themselves. The cavitation field that is being produced by a radially symmetric sound field burst of approximately 23 kHz onto the occlusion at high energy, thus damaging and/or breaking up the plaque.

The catheter device of the invention may be implemented using a low diameter catheter tube which includes a magnetic guidewire centering means surrounding the guidewire. This magnetic guidewire centering means uses unidirectional magnetic forces that force a guidewire comprising a magnetic element to float inside the catheter due to repulsion of magnetic forces evolving between said magnetic element and said magnetic guidewire centering means, thus stabilizing the guidewire (ensuring the guidewire will vibrate in a controlled direction and will not deviate in undesirable directions) thereby reducing friction and improving guidewire rotational movement abilities. This magnetic centering means may be either passive, i.e. comprising permanent magnets, or active, i.e. comprising a combination of permanent magnets and electromagnetic coil.

The device of the invention may further include a lumen for debris aspiration, and it may be further adapted to allow injection of fluids via the guidewire lumen, such as contrast media and/or cooled saline for temperature control.

The invention also provides a means for deflecting the driller tip into a desired in vivo direction thereby imparting additional maneuverability to the distal tip of the guidewire, when passing through complicated artery morphologies.

The catheter device of the invention may be equipped with a thermo-sensor mounted in the distal end of the catheter that is used to communicate temperature readings to the practitioner either via wires or wirelessly, from the distal end of the catheter to the proximal end.

The proximal end of the catheter device of the invention may be bifurcated to provide a first entrance for the drilling/sensing guidewire and an entrance for saline/contrast media or other fluid, the debris aspiration tube, the ultrasound transducer power cords and the thermo-sensor power/reading cords, if any.

The present invention also provides a method for opening occluded body passageways by means of a drilling guidewire, which may be a conventional guidewire that is slightly modified and which may be operated (upon physician selection) in an active mode (electrically powered) as a driller held by the catheter surrounding the guidewire near its distal end. Thereby, the physician can advance the guidewire as far as possible towards the occlusion while the device is in a passive mode, and upon reaching an occluded section switching the device into an active mode, thereby initiating a drilling process to allow further advancing the guidewire all the way to the distal end of the occlusion, and thereafter to treat the occluded passageways using conventional procedures, such as by means of balloon catheters and/or stents.

The Apparatus

The present invention is directed to an active guidewire housed in a magnetic catheter based device, to a method for opening obstructed body internal passages and for sensing and characterizing tissues and substances being in contact with the device of the invention.

In general, the device of the present invention comprises a coiled guide wire, capable of inducing magnetic force(s) therein while threaded through a catheter with fixed magnets attached to it. That magnetic force can be an alternating magnetic force, creating vibrations in the tip of the guidewire, wherein said vibrations of the guidewire are utilized for opening a passage through an occlusion.

An alternative apparatus comprises coiled guide wire threaded into a human vessel, which is positioned in a strong magnetic gradient flux. This magnetic gradient flux is generated by in-vitro magnetic apparatuses', such as strong fix magnets, or strong electro-magnets.

More particularly, the present invention relates to a device and method for in vivo drilling in living tissue and/or finding the weak path in the said living tissue, in body internal passages and body organs, which may be utilized for opening a passage suitable for passing a treatment device (e.g., a stent, balloon) through an occluded body internal passage (e.g., blood vessel), such as in cases of CTO. The in vivo drilling is performed by means of a drilling guidewire with an embedded electro-magnet, and more specifically a coil based electro-magnet section that aside from drilling through the occlusion enables the operator to sense the tissue/substance being in contact with the drilling part of the drilling guidewire. The sensing of the tissue/substance contacting the drilling guidewire may be advantageously used to provide an indication as to whether the drilling guidewire properly operates in the occluded internal passage or whether it deviates therefrom and injures the passage wall. The path drilled and or opened and or re-canalized through the occluding matter enables the passage of an either the special guidewire or another conventional guidewire through the occluded passage and thereby allows carrying out the conventional treatments of "over-the wire" applicable in such cases, such as, for example, by means of balloon catheters and stents.

The drilling according to this invention is based on an electro-magnetic force generated by the combination of feeding current through a guidewire according to the invention, threaded in a catheter with embedded magnets. The drilling itself is carried out by means of rapid vibrations e.g., at a frequency of about several dozens Hz, preferably in the region of 1-600 Hz, low amplitude vibrations e.g., with an amplitude of about a fraction of a mm, preferably in the region of 0.01 to 1 mm, that are directed in vivo to the occluding matter. The in vivo drilling device of the invention is designed to transfer the drilling energy with high efficiency into hard/calcified tissue, while keeping the efficiency low when drilling into relatively soft tissues. The drilling vibrations are preferably limited to low amplitudes, resulting in a drilling scheme that transfers energy very efficiently into hard/calcified occlusions. At the same time, such drilling cannot transfer energy efficiently into soft tissues, such as the artery wall, thus lowering the risk of perforation or dissection thereof.

The present invention also provides a method for opening occluded body passageways by means of a drilling guidewire, which comprises a conventional guidewire that is slightly modified and which is operated (upon physician selection) in an active mode (electrically powered) as a driller held by the catheter surrounding the guidewire near its distal end. In this manner the physician can advance the guidewire as far as possible towards the occlusion while the device is in a passive mode, and upon reaching an occluded section the physician switches the device into an active mode, thereby initiating an active magnetic drilling process to allow further advancing the of the guidewire all the way to the distal end of the occlusion, and thereafter to treat the occluded passageways using conventional procedures, such as by means of balloon catheters and/or stents.

The Guide Wire

A preferred guidewire according to the invention is based on a conventional configuration guidewire with the added capability of driving an electrical current through the coils that are a part of the guidewire.

In another embodiment of the invention, the coil already embedded in a conventional guidewire is electrically connected to an external current driving unit, thus creating a magnetic flux in the vicinity of said coil. When the coil is then inserted into a magnetic field gradient, an induced magnetic force is developed which acts on the coil. This magnetic field gradient may be generated either by in-vivo means, or by ex-vivo (external to the human body) means.

In yet another embodiment of this invention, the coils that are electrically connected to an external current driving unit are positioned at various places along the guidewire.

In a preferred embodiment of the invention, the coil is positioned at the front portion of the guidewire (i.e. in the region of its distal end). The exact position of the coil may vary from one embodiment to another.

In a further embodiment of the invention, the coil distal end is positioned approximately 50 mm before the distal tip of the guidewire.

In yet another embodiment of this invention, the coil distal end is positioned just at the tip of said guidewire.

In yet alternative embodiments of this invention, the coil distal end may be positioned along the guidewire at any distance, in the range of 10-300 mm away from the distal tip of the guidewire.

In yet another preferred embodiment of the invention, the coil may be divided into several gapped segments of coils, implemented in an optimized electro-magnet configuration to achieve a significant magnetic field flux along the guidewire.

In yet another preferred embodiment of the invention, the number of divided coil segments is typically in the range of 3 to 30.

All such segments can be connected in serial to each other, or in another electrical connection, which allows achieving the desired result.

In yet another preferred embodiment of the invention, the coils are connected in serial to each other in such a manner that the current direction changes from one coil to its neighboring coil. In short, assuming there are e.g. 7 coils, then all coils are connected in serial to each other, in a way that the current fed into coils 1, 3, 5 and 7 flows in "clockwise" direction, while the current fed into coils 2, 4 and 6 flows in "counterclockwise" direction.

In yet another preferred embodiment of this invention, the gap between adjacent coils will be of the order of 1-5 mm, while the length of each coil section may preferably be in the range of 0.5-10 mm.

In yet another preferred embodiment of this invention, the gaps between the coils section may be one of the following:
  Left empty.
  Filled with another passive coil, that is not connected to an electrical driving unit.
  Filled with other material, preferably a bio-compatible type of material.
  Filled with a thermal conductive material, to sink the heat dissipation generated by the coil into the metal inner member of the guidewire.

In yet another preferred embodiment of the invention, the coils are made of wire with diameter that is in the range of 25 to 100 microns (1 to 4 mils).

The coils are made of silver, copper, platinum, or any other material that is compatible for inserting into living organs of a human being.

In yet another preferred embodiment of the invention, the coil may be of a mechanical structure similar or identical to the mechanical structure already implemented in the guidewire, hence suitable for use in catheterization and/or treatment of live human beings.

In yet another preferred embodiment of the invention, the external diameter of the coil(s) is identical to the external diameter of the guidewire section, in which the coil(s) are embedded, typically in the range of 14 to 18 mils.

In yet another preferred embodiment of this invention, the coils are coated with isolating materials. Preferably these materials will provide clinical benefits, such as hydrophilic coating.

In yet another preferred embodiment of this invention, the coating may be of bio-compatible type, such as a Teflon based coating i.e., a polytetrafluoroethylene (PTFE) based coating.

In yet another preferred embodiment of this invention, the coils are connected to an external current driving unit, by means of two leads that are pulled along the guidewire up to its proximal side end. Optionally these leads can be threaded alongside the guidewire, wrapped in an isolating shrinkable sleeve, or through a hollow core of the guidewire. Alternatively, either of the leads can be a part of the core member of the proximal portion of the guidewire. It should also mentioned, that more than a single lead can be a part of the core member of the proximal portion of the guidewire, assuming it is designed in a way to be comprised of several electrically isolated cores aligned with each other. In this embodiment the leads are optionally terminated with a connector, preferably miniature connector, or as bare wires, directly connected to the external driving unit.

The present invention also provides a guidewire device, capable of electrically controlling its distal tip pushing force, according to the electrical current fed into the coils of the guidewire.

An oscillating current will result in an oscillating magnetic force, the magnitude of the force depending on the amplitude of the current fed.

A DC current will result in a constant magnetic force, which adds to the inherent mechanical force of the tip of the guidewire, hence changing its stiffness according to the current level.

The Catheter

The in vivo drilling of the guidewire according to the invention is achieved when threading the guidewire according to the invention into a magnetic catheter, and then feeding electrical current into the coils of the guidewire.

The catheter according to this invention may be any type of hollow tube.

Preferably, the hollow tube may be made for clinical use in general, and more particularly for use in coronary catheterization procedures.

In yet another preferred embodiment of the invention, the catheter is a conventional catheter provided with magnetic beads along it.

In yet another preferred embodiment of the invention, the magnetic beads are hollow beads, attached to the inner wall, the outer wall, or embedded in the wall of the catheter.

In yet another preferred embodiment of the invention, the magnetic beads are made of rare earth magnets, such as NdFeB grade 48. The preferred size of the said magnetic beads is preferably designed to match the design of the coils of the guidewire.

In an optional embodiment of the catheter according to the invention, the number of magnetic beads along a specific length of catheter equals the number of coil segments along same length of the guidewire.

Alternatively, the number of coils can differ from the number of magnetic beads. In this case the maximum magnetic force generated by the apparatus shall be maintained as long as coils are surrounded by magnetic beads.

In a preferred embodiment of the invention, each coil segment of the guidewire is surrounded by two magnetic beads attached to a catheter, in a manner that the magnetic field generated by the coil is positioned in a high gradient of the magnetic field generated by the two beads, hence producing a magnetic force.

In yet another preferred embodiment of the invention, the magnetic bead may be a hollow shaped cylinder, with outer diameter of 2.7 F(0.9 mm) and an inner hole diameter of 2.0 F (0.65 mm) with a length of 3 mm.

The frequency of the vibrations may be changed in close loop in order to manually or automatically reach the resonance frequency or anti-resonance of the whole apparatus, thus gaining continuous optimization of the drilling energy.

In yet another embodiment of the catheter according to the invention, the rare earth magnets of the catheter can act also as radio opaque markers, used for identification (automatically and/or manually) of the relative position between the guidewire and the catheter, and hence provide means to selectively drive coils that are overlapping the guidewire magnets. Such selective driving provides the following main advantages:

The power loss on the coils is lower relative to the power loss when activating all the coils (as only some of the coils are driven).

The working range of the magnetic force may be increased, relative to the working range when powering all of the coils.

The magnetic force level may be efficiently developed, as only coils that contribute to the magnetic power are activated, while other coils are selectively not powered.

Sensing

The electrical power (current and voltage vs. frequency) fed into the vibrating elements, can be analyzed to measure the overall apparatus magnetic impedance, and thereby provide an indication about the type of tissue/substance drilled, as described in Israel copending patent application No. 168569 and in copending application PCT12006/000541.

BRIEF DESCRIPTION OF THE DRAWINGS

The present invention is illustrated by way of example in the accompanying drawings, in which similar references consistently indicate similar elements and in which:

FIG. 1A shows a longitudinal and a cross-sectional view of a catheter device of the invention for opening occluded passageways by means of a vibrated magnetic field;

FIG. 1B illustrates a possible arrangement of magnets and electrically vibratable means;

FIG. 1C illustrates a catheter device of the invention for opening occluded passageways by mechanically induced vibrations and magnetic attraction forces;

FIG. 1D shows a possible guidewire structure of the invention having an embedded ferromagnetic section;

FIG. 2A illustrates a catheter device of the invention for opening occluded passageways by means of a magnetic field induced by a coil;

FIG. 2B illustrates a catheter device of the invention for opening occluded passageways by means of a magnetic field induced by a plurality of coils;

FIG. 2C illustrates a catheter device of the invention for opening occluded passageways by means of a magnetic field induced by a plurality of coils separately energized by a power source;

FIG. 2D shows a possible electrical activation scheme of the separate coils arrangement shown in FIG. 2C;

FIG. 3A shows a longitudinal and a cross-sectional view of a catheter device of the invention for opening occluded passageways by means of an electrical vibratable element;

FIG. 3B shows a longitudinal and a cross-sectional view of another embodiment of the catheter device of the invention for opening occluded passageways by means of an electrical vibratable element;

FIG. 4A illustrates a catheter device of the invention capable of centering a guidewire passing therein by means of fixed magnets;

FIG. 4B illustrates a catheter device of the invention capable of centering a guidewire passing therein by means of a fixed magnet and an electromagnetic coil;

FIG. 5A illustrates a guidewire of the invention comprising an acoustic impedance sensing means;

FIG. 5B illustrates a possible acoustic head arrangement of the invention;

FIG. 5C illustrates a possible structure of an acoustic transducer comprising a waveguide;

FIG. 5D exemplifies various signals that may be obtained via acoustic impedance sensing means; and FIG. 5E schematically exemplifies the operation of an acoustic transducer of the invention.

FIG. 6 illustrates a longitudinal view of another embodiment of the catheter device of the invention which is comprised of an outer conduit comprising an inner conduit, wherein a guidewire is threaded through the lumen of the inner conduit which is surrounded by miniature magnets, and wherein coils are wrapped around the outer conduit of the catheter.

FIG. 11A shows a close up cross-sectional look of the coils according to the invention, and FIG. 11B the magnetic flux developed thereby, FIGS. 13C and 13D show a typical magnetic field developed by the magnetic beads.

DETAILED DESCRIPTION OF PREFERRED EMBODIMENTS

Figure 7:
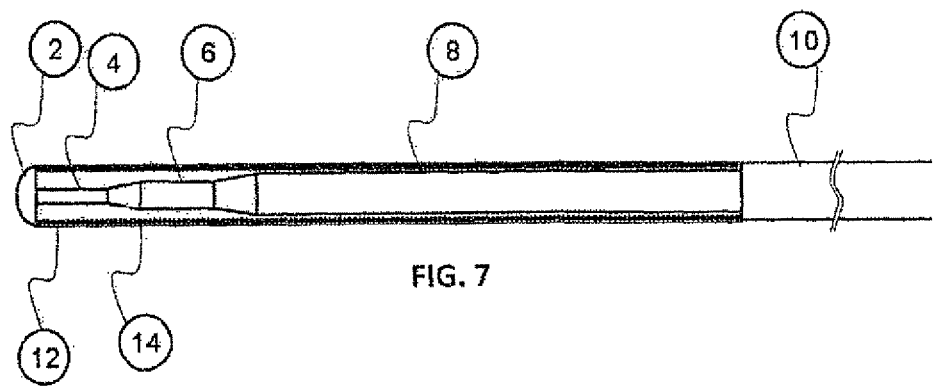
FIG. 7 shows the general structure a prior art guidewire.

FIG. 1 shows longitudinal and cross-sectional views of a device 201 designed for in vivo generating and transferring mechanical vibrations. The device 201 comprises a catheter tube 204 and a drilling guidewire 202 passing therethrough. Drilling guidewire 202 comprises miniature magnets 203 radially attached thereto near its distal tip. Catheter tube 204, comprising guidewire 202, comprises magnetic field inducing means 205 attached to the inner wall of catheter tube 204 near its distal end opening 204b. Magnetic field inducing means 205 may also be embedded in the wall of catheter tube 204 (not shown). In this preferred embodiment magnetic field inducing means 205 are implemented by a structure comprising fixed magnets, 205a and 205b, and vibratable (e.g., piezoelectric) elements 206, attaching the fixed magnets. Vibratable elements 206 are supplied with electrical power E(t) provided by electrical power source 208 via electrical wiring 207. Drilling guidewire 202 comprises magnetic coupling means implemented by miniature magnets 203 mounted near a distal end portion thereof.

Fixed magnets, 205a and 205b, and vibratable elements 206 are preferably hollow cylindrical elements configured to allow passage of a guidewire therethrough. Alternatively they may be embedded within guidewire 202. When operated in a drilling mode, an alternating electrical signal is supplied to vibratable elements 206 which in turn vibrate fixed magnets 205a and 205b, thereby inducing a vibrating magnetic field in the proximal end portion of catheter tube 204. Miniature magnets 203 are affixed near a distal end section of guidewire 202 such that when said distal end section of guidewire 202 is positioned within the structure comprising fixed magnets, 205a and 205b, and vibratable (e.g., piezoelectric) elements 206, a distal end portion of guidewire 202 protrudes outwardly via the distal end opening of catheter tube 204.

The structure comprising fixed magnets, 205a and 205b, and vibratable elements 206, connecting said fixed magnets may be attached to the inner wall of catheter tube 204 via magnet 205b, such that magnet 205a connected thereto via vibratable element 206 is maintained in the interior of the catheter in a more or less floating state, as exemplified in FIG. 1A. Alternatively, vibratable elements 206 may be attached to the outer wall of catheter tube 204, or be embedded therein (not shown). In a similar fashion additional magnets 205a may be attached by means of vibratable elements 206a, 206b and 206c, connected therebetween, to provide a structure of "floating" magnets 205a connected to magnet 205b, which is affixed to the inner wall of catheter tube 204, as exemplified in FIG. 1B. Similarly, said structure containing "floating" magnets 205a is free to vibrate in the guidewire lumen of catheter tube 204.

Guidewire 202 may be a conventional guidewire such as the Cordis Wizdom guidewire (Johnson & Johnson, USA), or more preferably may be a guidewire having medium distal stiffness, specially designed for treatment of CTOs such as the Pilot 50 manufactured by Guidant, USA. Miniature magnets 203, can be manufactured from rare earth materials such as NdFeb series, preferably from NdFeB grade 42 or higher, and they are preferably in the shape of miniature hollow cylinders attached to the guidewire 202, as shown in the cross-sectional view in FIG. 1A, or are embedded within the guidewire (not shown). The outer diameter of the magnets 203 should be configured according to the diameter of guidewire 202, for example, if the diameter of guidewire 202 is about 0.36 mm (14 mils), then the outer diameter of miniature magnets 203 may generally be in the range of 0.5 to 1.0 mm, preferably about 0.7 mm, while their inner diameter should match the guidewire diameter or will be reduced down to zero in the case they are embedded in the wire. The thickness of the miniature magnets 203 can vary and reach several mm, all in accordance to the guidewire they are attached to and or embedded within. For example, the length of miniature magnets 203 may generally be in the range of 1.0 to 5.0 mm, preferably about 2.5-3.0 mm.

The distal end portion of guidewire 202 is preferably made of a material that is softer or less stiff, in relation to the other portions thereof in order to allow it to collapse and in this way to avoid any possible damage, such as perforation or dissection to the arteries wall. Miniature magnets 203 are preferably affixed on a distal section of guidewire 202, near its distal end portion. While in the above examples, and in the figures, miniature magnets 203 and guidewire 202 are concentric, and the intervals between miniature magnets 203 are of equal length, the invention may also advantageously utilize different configurations. For example, miniature magnets 203 may be mounted on guidewire 202 in a non-concentric form and the interval between miniature magnets 203 may be of different lengths.

Similarly, the geometrical dimensions of fixed magnets, 205a and 205b, and vibratable elements 206 should be adjusted according to the inner radius of catheter tube 204. For example, if the inner diameter of catheter tube 204 is about 1.0 mm, then the inner diameter of fixed magnets, 205a and 205b, may generally be in the range of 0.7 to 0.9 mm, preferably about 0.8 mm. Fixed magnets, 205a and 205b, can be manufactured from rare earth materials such as NdFeB series, preferably from NdFeB grade 42 or higher, and vibratable elements 206 is preferably a type of piezoelectric element such as manufactured by APC.

By applying voltage of the order of several dozens of Volts to the opposite ends of the piezoelectric element, said element bends and straightens at an amplitude of a fraction of a mm, hence changing the magnetic field surrounding the magnets attached to guidewire 202. This change in the magnetic field causes evolution of a magnetic force of the order of up to several grams.

FIG. 1C is a longitudinal view of a device 211 of the invention in which the proximal end of guidewire 220 is held by mechanical means 221, capable of repeatedly applying rapid longitudinal pulling forces (designated by arrow 224) thereto. Mechanical means 221 may be implemented by several methods, for example by connecting guidewire 220 to an external vibratable element, such a piezoelectric transducer, activated by a suitable electrical powering signal. Catheter tube 222 includes a series of fixed magnets 223a, 223b, 223c, . . . , affixed to (or alternatively embedded in, not shown) the inner wall of catheter tube 222. Internal magnets 223a, 223b, 223c, . . . , are preferably hollow cylindrical magnets configured to apply distally pulling forces (designated by arrow 225—pulling towards the distal end of the guidewire) on miniature magnet 203 affixed to (or embedded in, not shown) guidewire 220. External mechanical means 221 applies repeated rapid pulling force 224 which due to the distal attraction applied by fixed magnets 223a, 223b, 223c, . . . , results in rapid longitudinal vibrations of the distal tip of the guidewire 220.

Fixed magnets 223a, 223b, 223c, . . . , can be manufactured from rare earth materials such as NdFeB, preferably from NdFeB grade 42 or higher. The outer diameter of fixed magnets 223a, 223b, 223c, . . . , should be set according to the inner diameter of catheter tube 222. For example, if the inner diameter of catheter device is about 1.0 mm, then the outer diameter of fixed magnets, 223a, 223b, 223c, . . . , may generally be in the range of 0.7 to 0.9 mm, preferably about 0.8 mm.

FIG. 1D shows a possible preferred embodiment of a guidewire 234, which is equipped with a segment 234a comprising ferromagnetic and/or magnetic portions 235 embedded therein, thereby creating a ferromagnetic and/or magnetic segment 234a, which diameter is not larger, or only slightly larger, than the original diameter of the guidewire 234. This ferromagnetic and/or magnetic segment 234a, when inserted into a magnetic field gradient is subject to magnetic forces. Of course, the number of ferromagnetic and/or magnetic portions 235 provided in guidewire 234 may be different than that exemplified in FIG. 1D.

FIG. 2A illustrates a catheter device 210 of the invention which is capable of generating an alternating magnetic field in a lumen thereof by means of an electromagnetic coil 215 wrapped on the inner wall of catheter tube 204. Alternatively, coil 215 may be externally wrapped on the outer surface of catheter tube 204, or embedded inside the catheter wall. Coil 215 is preferably located near the distal end opening of catheter tube 204, and it is activated by an electrical current supplied thereto by means of electrical wires 217 and 218 electrically connecting it to electrical driving unit 213. Coil 215 is preferably a wrapped wire made from a flexible and electrically conducting material, preferably from copper, and coated with a type of a bio-compatible material, preferably parylene. The diameter of said wrapped wire may be in the range of 0.02 to 0.25 mm, preferably about 0.1 mm. The number of turns of coil 215 may vary according to the implementation specific requirements. For example, in one possible embodiment of the invention the number of turns of coil 215 may be in the range of 30 to 150 turns. The axial length of coil 215 should be adjusted according to the length of the section of guidewire 202 comprising the miniature magnets e.g., about 10 mm.

FIG. 2B illustrates a catheter device 212 of the invention comprising catheter tube 226 equipped with several coils 227, 228, 229, 224, positioned near its distal end and arranged in a Helmholtz like configuration. Coils 227, 228, 229, 224, may be wrapped on the inner wall of catheter tube 226, on its outer surface, or alternatively embedded inside the catheter wall. Guidewire 230 passing in the lumen of catheter tube 226 comprises miniature magnets 231, 232, 233, . . . , attached thereto. The location of the coils 227, 228, 229, 224, and magnets 231, 232, 233, . . . , in catheter device 212 is preferably configured to provide segments of adjacently located pairs of coils together with a magnet. For example, coils 227 and 228 may surround magnet 231, coils 228 and 229 may surrounds magnet 232, etc. Upon excitation of the coil pairs a gradient of magnetic field is generated in between the coils. When this gradient is generated near the fixed magnets 231, 232 and 233 a magnetic force is excited. In the embodiment shown in FIG. 2B, the current in coils 227 and 229 may be in a clockwise direction, while the current in coils 228 and 224 may be in a counterclockwise direction. The magnets, may then be positioned such that the north poles of magnets 231 and 233 are at the distal side of the magnets, while the north pole of magnet 232 is at the proximal side thereof. Using such an arrangement achieves a multiplication of the magnetic force operating on a single magnet. The multiplication factor is determined by the number of coil/magnet segments. It goes without saying that a different number of coil/magnet segments, other than the three segments shown in the FIG. 2B, may be employed.

For example, an apparatus including 4 coils (3 segments), each having 34 turns, which are being fed with a 1 A electrical current, can produce a force of 3 grams when measured on 3 miniature magnets, the length of which is about 3 mm, and having an outer diameter of about 0.8 mm and an inner diameter of about 0.4 mm.

FIGS. 2C and 2D demonstrates an operation/excitation scheme of a catheter device 212 in which the coils 237a, 237b, 237c, . . . , provided in the catheter tube 226 are separately powered via respective wires 238a, 238b, 238c, . . . , electrically connecting said coils to an external power source 239, such that each coil may be operated independently. While it is possible to operate/excite all of the coils 237a, 237b, 237c, . . . , that surround the guidewire 230 (not shown in FIG. 2C) in phase (meaning the powering electrical current is fed to all coils simultaneously) it is also possible to excite the coils in series one after the other, as exemplified in FIG. 2D.

FIG. 2D graphically illustrates the currents Ia(t), Ib(t), Ic(t), . . . , supplied to coils 237a, 237b, 237c, . . . , respectively in such a possible activation scheme. This activation scheme provides the coils with "wave" like current. The magnetic field is consequently developed in a wave like manner—providing a relatively high duration magnetic field that propagates along the catheter tube 226. Inserting a guidewire 230 (such as shown in FIG. 2B) results in an apparatus that provides relatively constant magnetic force along relatively long range along the catheter/guidewire axis.

Additionally, by measuring the coil ohmic resistance (the instant ratio between the voltage developed on the coil and the current fed through the coil), one can deduce the temperature of the ambient surrounding the coils.

Advantageously, coils 237a, 237b, 237c, . . . , may be designed such that the direction of the activation currents of adjacent coils (e.g., Ia(t) and Ib(t)) are of opposing directions in order to generate magnetic field gradients in the lumen catheter tube 226. The distances between coils 237a, 237b, 237c, . . . , may be of different lengths in order to provide varying distances between the magnetic field gradients.

Clearly, other waveforms different than those shown in FIG. 2D, may be fed into the coils, where the number of coils may again differ from the 3 coils shown in FIG. 1A.

FIG. 3A shows longitudinal and cross-sectional views of a catheter device 240 comprising a vibratable guidewire 244 designed for in vivo generating and transferring of acoustical (and/or other type of) vibrations. Guidewire 244 passing inside guidewire lumen 242, comprises an ultrasonic (or another type of) vibrating element 247 that may be used for in vivo inducing vibrations (e.g., acoustic vibrations) and/or for sensing and characterizing the substance/tissue that is in proximity to the distal end of the guidewire device 244. Guidewire lumen 242 may be also used for injection of liquid, such as cold saline or contrast media. Catheter tube 241 further comprises a debris aspiration lumen 243 and a thermo-sensor 246. At the proximal end of catheter tube 241, there are shown power wires 247w, of the vibrating element 247, and wires 246w connecting to the thermo-sensor 246. Of course, wires 246w are absent when the device according to the invention does not include a thermo-sensor. Wires 246w and 247w are connected to a control unit 248 capable of inputting thermal readings from thermo-sensor 246, providing powering signals to vibrating element 247, and inputting and analyzing signals produced by vibrating element 247.

FIG. 3B shows longitudinal and cross-sectional views of a catheter device 240b comprising a vibratable guidewire 244 designed for in vivo generating and transferring of acoustical and/or other type of vibrations. The operation of catheter device 240b is similar to that of catheter device 240. The structure of catheter device 240b is, however, different in that the guidewire lumen 242b is concentrically located in the debris aspiration lumen 243b.

FIG. 4A illustrates a possible arrangement for a catheter device 265 capable of centering a guidewire 261 passing therethrough by means of fixed magnets, 260 and 262. Fixed magnet 260 is preferably a hollow cylindrical magnet attached to the inner wall of catheter tube 263 (or embedded in it, not shown), such that guidewire 261 can be freely moved longitudinally therethrough. Fixed magnet 262 is affixed to guidewire 261 at a location corresponding to the location of fixed magnet 262 in catheter tube 263. Fixed magnets 260 and 262 are designed such that repulsion forces caused due to their opposite magnetic polarities centers guidewire 261 inside catheter tube 263 when positioned therein in its operative state, as exemplified in FIG. 4A. In similar way, in FIG. 4B guidewire 261 is centered inside catheter tube 263 by means of electromagnetic coil 265. Coil 265 may be activated once guidewire 261 is positioned in an operative state in catheter tube 263 by supplying it electrical current via conducting wires electrically connected to it.

FIG. 5A shows a conventional guidewire 252 comprising one or more miniature acoustic and/or other transducers 256 which are fed with electrical power provided by electronic unit driver 253 electrically connected thereto by means of electrical wires 254. Electronic unit driver 253 is advantageously designed to provide various electrical supply signals, in particular it may be able to supply direct current (DC) and alternating current (AC) in high frequencies.

FIG. 5B shows a preferred embodiment of the acoustic or other transducer 257 of guidewire 252. Acoustic or other transducer 257 comprises an active part 250, such as a piezoelectric module, which is fed via wires 254 electrically attached thereto. Active part 250 is packed in an acoustic\vibrating head 251. Head 251 can provide readings that may be used to characterize tissue/substance 258 which it is acoustically or physically touching, and/or which is in its proximity. The design and construction of acoustic head 251 may vary from one embodiment to another, depending on the tissue/substance 258 in proximity thereto.

FIG. 5C shows another embodiment of a transducer (e.g., acoustic transducer) of the invention in which the active part 250 (that may be a piezoelectric transducer) is coupled to head 251 (e.g., acoustic head), via a waveguide 259 (e.g., acoustic waveguide). Conducting wires 254 are used to provide electrical supply to active part 250, and to output signals read from active part 250 that may be used to characterize tissue/substance 258 with which it is in contact, or in its proximity. It should be mentioned that waveguide 259, may carry both longitudinal waves, and/or transverse waves or both, and it may be built either in hollow configuration or solid one, with different lengths as implied by the specific implementation of this embodiment. Guidewire 252 may be a conventional cardiac coronary guidewire as commonly used in coronary catheterization procedures.

When the guidewire reaches a lesion difficult to pass, the sensing tip is activated and transmits acoustic or vibrating energy into the problematic lesion. The impedance of that lesion is relative to the type of occlusion reached. Thus the practitioner can determine whether he reached a healthy part of the artery (touching the vessel wall for instance) or a diseased portion, i.e. a calcified/fibrotic and/or other type of occlusion.

The interpretation of the occlusion reached is done by remotely analyzing the acoustic impedance of the material that is in proximity to the guidewire tip. A schematic reading for that acoustic impedance is shown roughly in FIG. 5D. Items 276, 277 and 278 represent acoustic impedances of different substances/tissues that were measured in proximity to the guidewire tip.

FIG. 5E illustrates the physical mechanism of the acoustic transducer of the invention. In any embodiment used, and under certain physical estimations, the behavior of the acoustic transducer, and its interaction with the substance/tissue it is in proximity with is as illustrated in FIG. 5E.

The left side, designated by numeral 260, is the electrical equivalent of the acoustic transducer. It comprises an electronic unit driver 263 connected to the acoustic transducer.

The electrical characteristics of the acoustic transducer are described by an LC circuit, 267 and left part of transformer 268.

The transformation of the electrical energy into the mechanical movement/energy of the transducer (that then creates acoustic energy) is effected by transformer coupling 268. The right side of transformer 268 provides the energy to activate the acoustic transducer. In the case of most acoustic transducers, and specifically in piezoelectric type transducers, the energy is fed into them is converted into mechanical movements. Parts 269 and 261 represent the construction of the transducer itself.

A capacitor 289, connected in series with inductor 281, provides a simple apparatus, with a single resonance frequency. This representation can then be used to represent an acoustic transducer up to the first resonance (but it gives a simple illustration to the physical mechanism). In the acoustic domain, the velocity and the force which represent the mechanical characteristics of the transducer correspond to the current and voltage, respectively of capacitor 289 and inductor 281.

Since there is always loss of energy, the device includes resistor 284. The interaction of the acoustic transducer with the tissue sensed is represented by 282.

When the transducer apparatus is operated, it receives the activating energy from the electronic unit driver 283, and in response it mechanically moves parts 289 and 81 which create an acoustic energy, some of which is transferred to resistor 84, while the rest penetrates into the tissue 282.

The "load" induced by the tissue (the equivalent acoustic load of 282) influences the behavior of the system. It actually changes the relationship between the velocity and power of the acoustic transducer, which is correlated to the voltage and current of the driver.

It is then possible to measure the electrical impedance (ratio between voltage and current) at the left side of the apparatus 280, and estimate the acoustic impedance of the right side 286.

Again, the acoustic impedance depends on the mechanical characteristics of the acoustic transducer (parts 289 and 281), the efficiency of the acoustic process 284 and the acoustic characteristics of the tissue 282 which is in proximity to the transducer. Thus, by estimating the acoustic impedance of the apparatus, it is possible to derive the acoustic characteristics of the tissue to sense.

It should also be mentioned that other equivalent schemes for apparatus containing acoustical transducers may be used. Some of those alternative schemes may be found in the existing technical literature, for example in "introduction to Theory and Design of Sonar Transducer", written by Oscar Bryan Wilson and published by Peninsula Publishing, Los Altos Calif., USA—1985.

FIG. 6 shows another embodiment of the invention comprising a catheter device capable of vibrating a conventional guidewire passing therein. In this embodiment the catheter device 298 comprises at least two conduits: An outer conduit 291 and an inner conduit 293. Guidewire 300 is threaded through the lumen of the inner conduit 293, and a distal end portion thereof emerges via the distal end opening of outer conduit 291 of catheter device 298.

Several magnets 290, 304 and 306 are attached around the outer surface of inner conduit 293. The length of magnets 290, 304 and 306 may be in the range of 1.0 to 5.0 mm. Magnets 290, 304 and 306 may have a hollow cylindrical shape having an outer diameter in the range of 0.5 to 1.5 mm, and an inner diameter that matches the outer diameter of conduit 293. Coils 292, 294, 295 and 296, wrapped over the outer surface of outer conduit 291, are made from a type of electrically conducting material, preferably from a copper wire coated with a bio-compatible material, preferably parylene, wherein the wire diameter is in the range of 0.05 to 0.25 mm.

The diameter of the inner conduit 293 of catheter 298 is designed to tightly fit over the outer surface of guidewire 300, thereby forcing guidewire 300 to axially move distally and proximally in a longitudinal direction. The diameter of inner conduit 293 may generally be in the range of 0.4 to 0.6 mm.

When activating coils 292, 294, 295 and 296 via an external driver 302, a magnetic field is induced, which in effect introduce a magnetic force acting on magnets 290, 304 and 306. Alternating the current fed into these coils results in alternating the magnetic force acting on the magnets, which in turn results in vibrations of inner conduit 293 relative to outer conduit 291 of catheter 298. Since the inner conduit 293 clamps guidewire 300, guidewire 300 is forced to vibrate as well.

While in the example shown in FIG. 6 coils 292, 294, 295 and 296, are wrapped externally (on the outer surface of outer conduit 291), they may as well be wrapped internally on the inner wall of outer conduit 291, or embedded in its wall. Similarly, magnets 290, 304 and 306 may be embedded into the wall of inner conduit 293.

FIG. 7 shows a typical prior art guidewire. Generally speaking the guidewire is divided into 2 main zones, a working zone 8, that are inserted into a vessel in the human body during a typical procedure carried out by a practitioner and the rest of the guidewire 10, which in most cases does not touch the vessel walls, as it is typically housed in a catheter. The overall length of typical guidewires varies in the range of about 160 to 300 cm. The working zone 8, is divided into several segments. The front tip 2 of the guidewire, is the first part of the guidewire that touches the organ, and must be designed in a way so as to not harm the organ or vessel wall. A first core member 4, follows the distal tip of the guidewire, surrounded by a spring type envelope 12. The section that contains the core member 4, typically sets the flexible zone of the guidewire enabling it to propagate safely and conveniently through the vessel. A thicker second core member 6, follows the first core member 4, forming a less flexible zone also called "stent zone". Second core member 6 is connected to a third core member, which is thicker and stronger and is used to enable the pushing of the guidewire along the vessel. Some guidewires may include different numbers of zones than described in this figure, e.g. to fit special clinical needs, yet this description gives a comprehensive structure of a typical guidewire. All core members are sometimes surrounded by spring type coils 12. The spring type coils 12 cover is may in some cases be coated with special coatings, such as hydrophilic coating 14.

Figure 8:
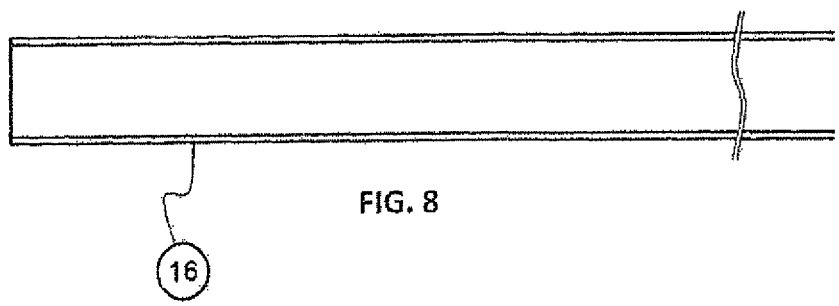
FIG. 8 shows a general structure of a prior art catheter.

FIG. 8 shows a typical structure of a prior art catheter 16. The catheter 16 in a typical case forms a hollow plastic tube, capable of being inserted into human arteries. This hollow structure enables the transmission of materials, e.g. liquids, and devices, e.g. the guidewire, through its inner lumen.

Figure 9A:
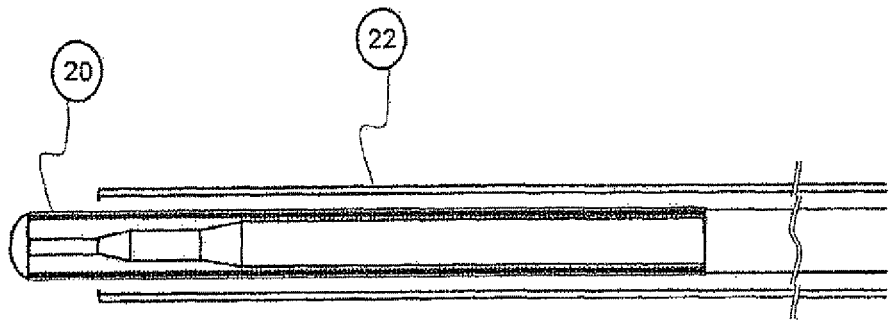
FIGS. 9A and 9B show a general typically usage of the prior art guidewire, when threaded for clinical treatment through a prior art catheter.
Figure 9B:
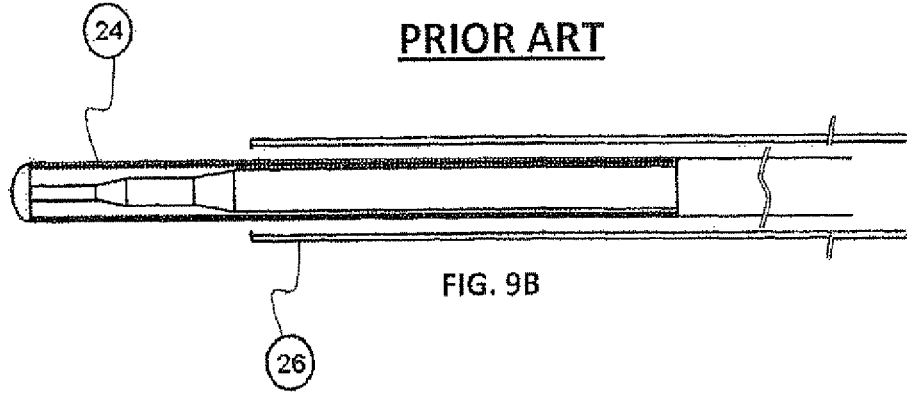

FIGS. 9A and 9B show the typical relation between a guidewire, as shown in FIG. 7 and a catheter as shown in FIG. 8. The guidewire 20 is threaded through a catheter 22, and then pushed towards the obstructed vessel to enable the treatment. It is typically capable of being to push back and forth guidewire 20 relative to catheter 22. FIG. 9B illustrates that sliding capability, where the guidewire 24 emerges to a significantly greater extent from catheter 26 than is shown in FIG. 9A.

FIG. 10 show a preferred embodiment according to the invention. FIG. 10A shows a guidewire 34 having similar sections/zones as a prior art guidewire, however the guidewire includes segmented coils 40 as a part of the overall coil cover 38 of the guidewire 34. It can be seen that the guidewire is built in a typical structure: A distal tip 30, followed by a flexible zone core member 32, followed by a thicker core member 36 (called the "stent zone"), and finally a thicker core member 42, followed by the rest of the guidewire 44. The coils covering the different zones, are no longer unified and passive as in the prior art, but rather include several sections 40, that are electrically connected to each other, and can transmit electrical current, hence generating a magnetic flux.

Figure 10A:
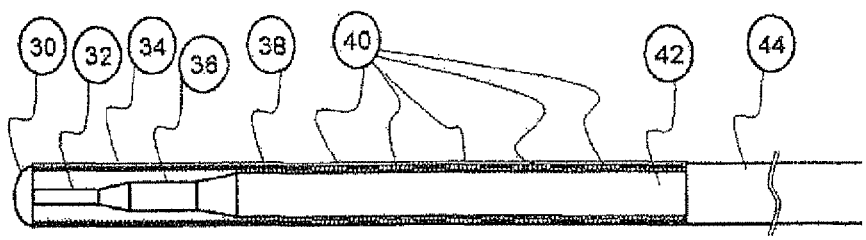
FIGS. 10A, 10B, 10C and 10D show a preferred guidewire embodiment according to the invention.

FIG. 10A shows that the active coil sections 40 cover the core member 42, containing 5 separate members.

Figure 10B:
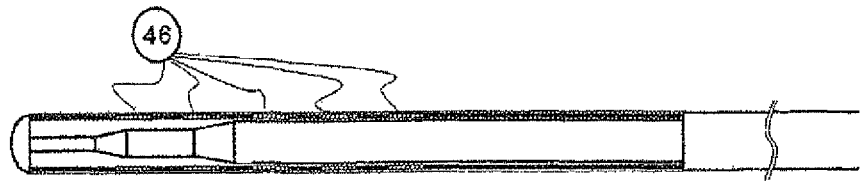

FIG. 10B shows a similar embodiment, however the active coil segments 46 are positioned more distally along the guidewire. The number of the separated segments in this figure is again 5.

Figure 10C:

FIG. 10C shows another typical embodiment, where the number of active coils sections 48, is 4.

Figure 10D:
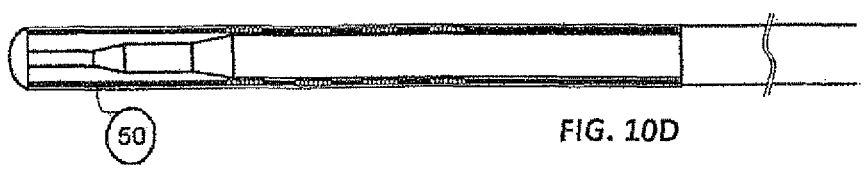

FIG. 10D shows another typical embodiment, where the active coil sections are not embedded in the passive coil section, as shown in FIGS. 10A, 10B and 10C, but rather the gaps between the active coils are filled with other types of materials 50, preferably bio-compatible materials.

It is apparent to the man skilled in the art that both, the exact position of the active coils, as well as the number of active coils, may be varied.

FIG. 8A shows a magnified cross section of 5 single layer coil segments. The coils are electrically connected in serial to each other in such a manner so that the direction of the current in coils 60, 64 and 68 is clockwise, while the current in coils 62 and 66 is counter clockwise. The resulting magnetic flux vs. the position along the guidewire is schematically shown in FIG. 8B. Other electrical connections between the coils are may be provided, resulting in different magnetic flux behavior. It is apparent to the man skilled in the art that the number of coils, number of layers for each coil, as well as their electrical connection may be varied.

Such configuration may be adapted to the guidewire as shown in FIG. 10 and FIG. 12.

Assuming such configuration is indeed adapted to the guidewire shown in FIG. 10, it will result in a variable magnetic field along the guidewire section enveloped by the active coils.

Figure 12A:
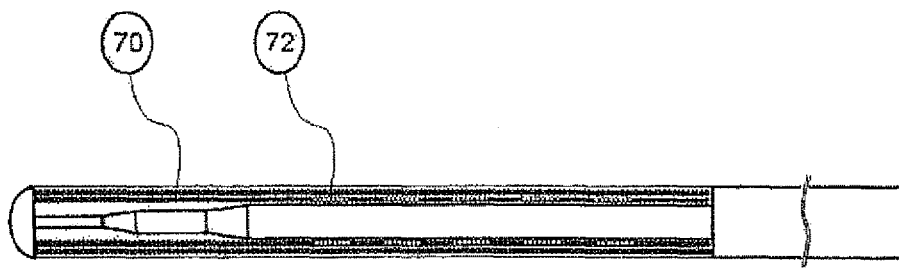
FIGS. 12A and 12B show other configurations of the guidewire.
Figure 12B:
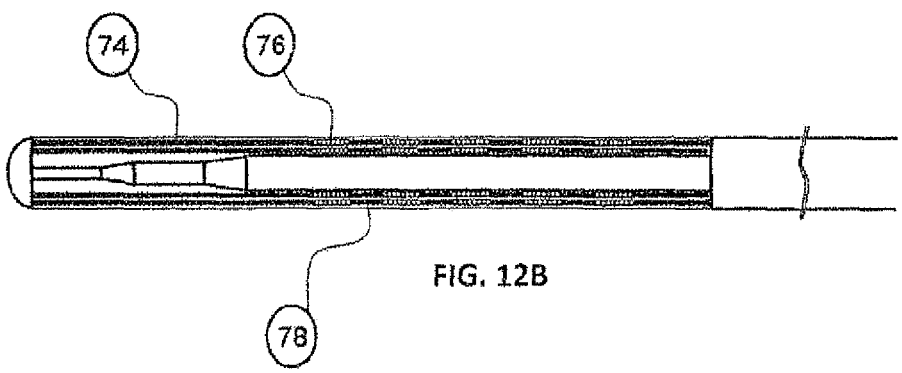

FIG. 12 shows two additional alternative embodiments for implementing the active coils into the guidewire 74. FIG. 12A shows a configuration where the active coils 72 are formed in a single layer, covered by a passive coil layer 70. FIG. 12B shows active coils segments 76 of two layer each, the gaps between active segments being filled with two layers of passive coils 78. Dual (or more then single) layers of active coils 76 result in higher (approximately double) magnetic flux generated by the coils, however it also results in s the guidewire to be thicker than if it had only a single layer.

Figure 13A:
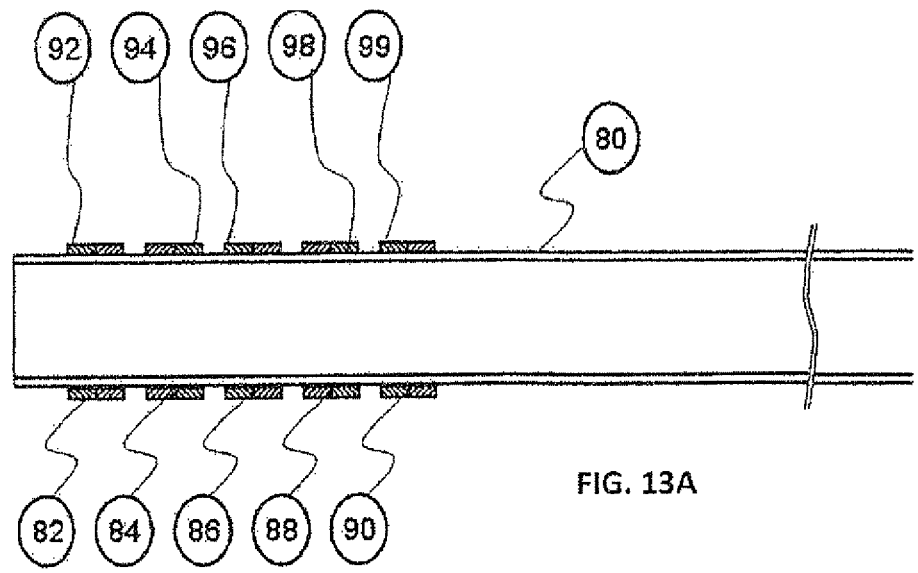
FIGS. 13A and 13B show the catheter according to the invention with magnetic beads.
Figure 13B:
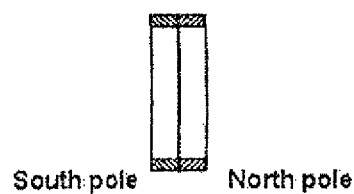

FIG. 13 shows a preferred embodiment of a magnetic catheter 80. FIG. 13B shows a hollow cylinder shaped magnet, having a north and south magnetic poles on opposite facets of the cylinder. The magnet bead preferably is made of rare earth magnetic materials such as NdFeB grade 48. A series of such beads, are attached to a catheter as shown in FIG. 13A. In this figure five beads (82,84,86,88 and 90), are attached externally to catheter 80. In this preferred embodiment the direction of the beads is shown schematically in the figure: faces 92, 94, 96, and 99 are the south poles of the magnets, while the opposite faces of each magnet is the North Pole.

The dependency of the gradient of the magnetic field on the gap between the magnetic beads is shown in FIGS. 13C and 13D. FIG. 13C shows the an apparatus of 2 magnetic beads separated 0.5 mm from each other 83, the resulting magnetic field is shown in graph 85.

FIG. 13D shows the magnetic beads 87, separated 2.0 mm from each other, the resulting magnetic field is shown in graph 89. These alternatives shown in FIGS. 13C and 13D, generates a relatively high magnetic field gradient, necessary to generate magnetic force.

However it should be emphasized that different number of magnetic beads, other orientation of the magnets as well as other dimensions of the gaps (either equally or not equally gapped) are covered by this invention.

Figure 14A:
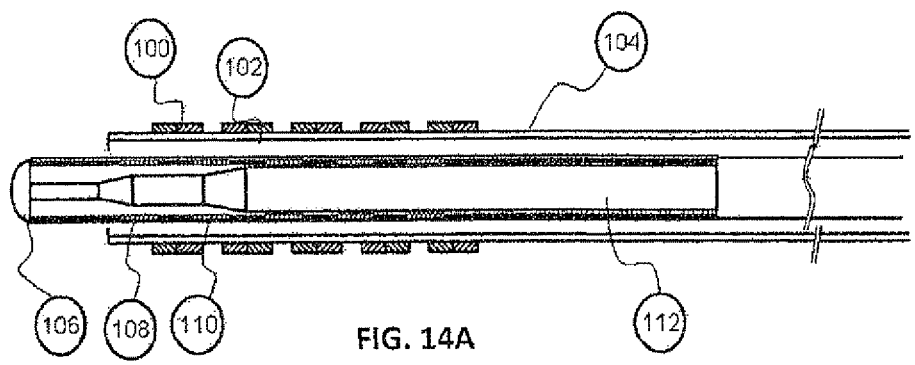
FIGS. 14A and 14B show a use of the guidewire when threaded via the catheter, to enable the desirable active drilling of the apparatus.

FIG. 14 shows a guidewire threaded via the catheter. FIG. 8A shows a specific optional positioning of the guidewire 112, inside the catheter 104. The maximum magnetic force will be developed once the magnet coil 110 is exactly in between two magnetic beads 100 and 102. The usage of several magnets, having a certain gap, and several coils having the same period as the magnets, will result in multiplication of the magnetic force accordingly. Other configurations of the magnet/coil arrangement may also be employed.

Figure 14B:
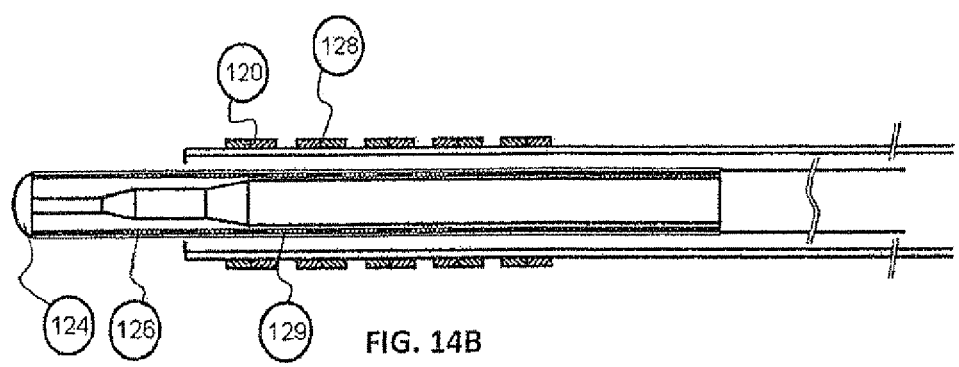

FIG. 14B shows a different positioning of the guidewire inside the catheter, where coil 129 is overlapped by magnet beads 128 and 120.

In both cases a magnetic force is developed on the active coils of the guidewire. Upon driving the coils with alternating current, the magnetic force is alternating, resulting in longitudinal vibrations of the guidewire and hence the guidewire tip 124.

Theoretically, if the system would be perfectly symmetrical (i.e. the guidewire is exactly in the middle of the catheter), then the magnetic force would be purely in the longitudinal direction. However, as the guidewire is free to move inside the lumen of the catheter, and in most cases the guidewire and the catheter are bent while inserted into human vessel, the configuration deviates from symmetrical, resulting in a magnetic force that also has lateral components.

Figure 15:
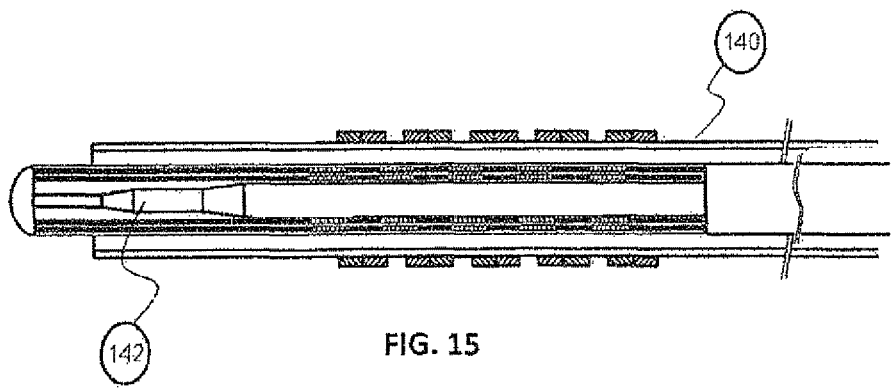
FIG. 15 shows another drilling apparatus based on the guidewire and the catheter.

FIG. 15 shows another combination a guidewire and a catheter. In this embodiment a double layered guidewire 142 is threaded via a catheter 140. The principle of generating magnetic force in this apparatus is similar to that described in FIGS. 5A and 5B.

Figure 16:
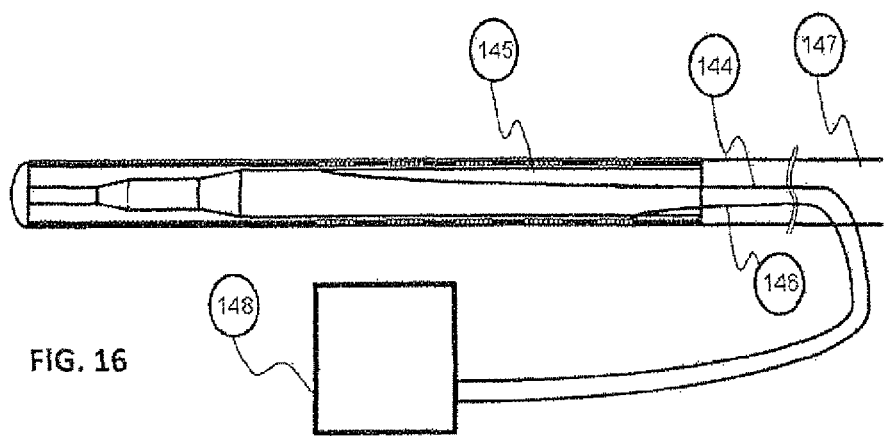
FIG. 16 shows the leads connecting the guidewire to the external current driver.

FIG. 16 shows the leads emerging from the active coils, and strung along the guidewire all the way to its proximal side. In this figure, the active coils are connected in serial to each other, where only two leads 144 and 146 are reach the proximal side of the guidewire. These two leads are then connected to an electrical current driver 148. When current is driven through the leads, a magnetic field is generated by the coils and induces a magnetic force. There are several possibilities to string the leads from the coils to the proximal guidewire, one being externally to the guidewire itself. A second possibility is to make the guidewire itself hollow inside, enabling the wiring of the leads through this lumen. Alternatively, since in a typical guidewire the core member of the guidewire 147 that follows the coils section 145 of the guidewire, is made of conductive material, it can be split into two parallel core members, electrically isolated from each other, where one serves as the positive lead, while the second, one as the negative lead.

At the proximal side of the guidewire the leads (of any type) can either end as bare leads—directly connected to the external electrical current driver, or make use of a connector, preferable a miniature connector, for ease of operation.

It should be noted, that the number of the leads may also be greater than two, and depends on the number of the independent coil segments implemented in the distal portion of the guidewire.

Figure 17:
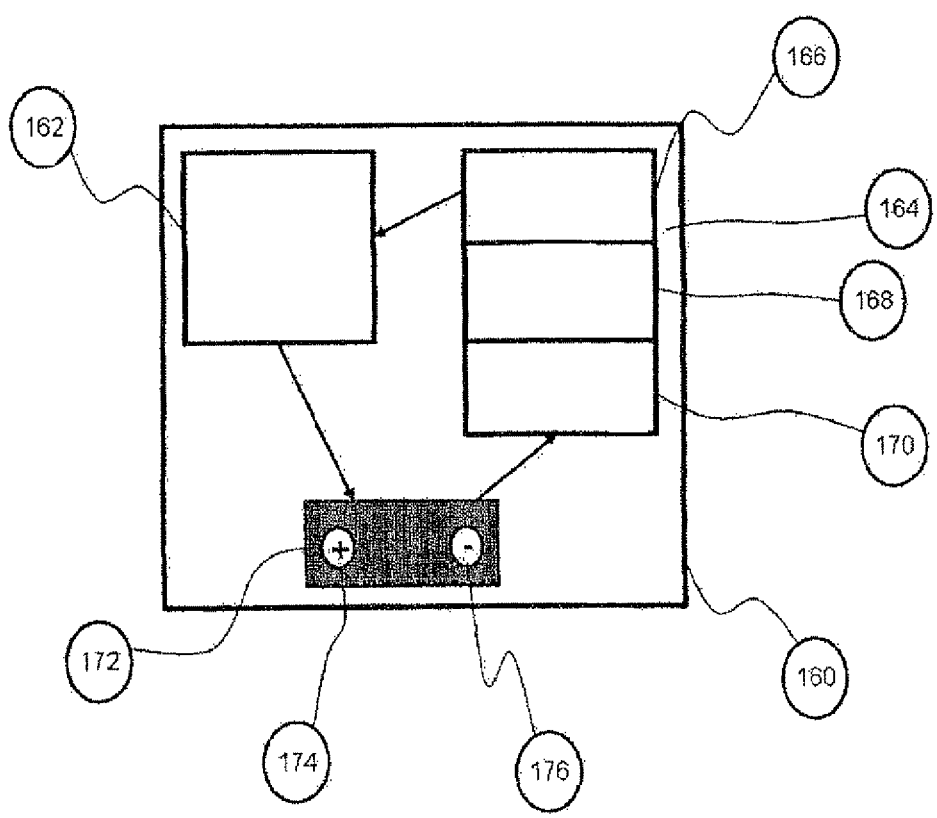
FIG. 17 shows a schematic block diagram of an external driver unit.

FIG. 17 shows a schematic configuration of the external current driver, and its derived capabilities.

The external driver 160, generally comprises the following modules:

A termination module 172, used to connect the leads of the guidewire by providing a positive and a negative signals, 174 and 176 accordingly.

A signal output generator 162: The current fed through these terminations to the guidewire is generated by a signal output generator 162. The figure illustrates a single signal generator, although multiple generators are may also be employed, connected to multiple termination modules. This generator can provide current into the guidewire coils, at different amplitudes, frequencies, and shapes. Preferably the output signal generator will provide sinus, rectangle, and triangle signals, at amplitude of up to 10 amperes, and frequencies at the range of 5 to 1000 Hz.

A signal analyzer comprising of three main submodules:

Signal input module 170. Responsible for sensing the current fed into the coils, while measuring the voltage developing on said coils, at different frequencies.

A signal analyzing module 168. Responsible to analyze the measured signals delivered by the signal input module 170. Such analysis is done by means of digital signal processing. More specifically the signals delivered from the signal input module 170, can be used to measure the following parameters:

The resistance of the coils. Since the resistance of the coils depends in a known manner on the temperature that surrounds the coil, it is therefore possible to remotely measure and analyze the temperature of the coils, and upon reaching a predetermined temperature limit, to automatically control the auto/manual control module 166 to stop output signal delivered by the signal output generator 162.

The impedance of the coils vs. the frequency of the signal fed into the coils, hence providing data about the organ that is in proximity of the guidewire tip that may be used for increasing the safety of the drilling feature of the guidewire. More particularly, usage of such continuous measuring of the impedance of the coils can be employed to determine whether the guidewire has dissected into the vessel wall, or may be even performing perforation to the vessel wall.

An auto/manual control module 166. Which receive the analysis from the signal analyzing module 168, which enables for automatic and/or manual control of the signal output generator 162. In the manual control mode the operator/physician can control the driver in various ways, such as using a keyboard to enter controlled parameters, leg pedal to start/stop the driver, rotating knob etc. The automatic mode enables some or all of the manual functions to be performed automatically, and hence reduces the work load of the physician. For example, upon analyzing a too high temperature developing on the active coils, the driver automatically stops its operation, until temperature returns to normal/allowed level.

It should be mentioned that although only a single signal output is shown in the drawing, multiple outputs may be employed enabling the simultaneous and independent driving of several coil leads.

All of the above mentioned parameters are given by way of example only, and may be changed in accordance with the different requirements of the various embodiments of the present invention. Thus, the abovementioned parameters should not be construed as limiting the scope of the present invention in any way. In addition, it is to be appreciated that the different tubes, wires, magnets, and other members, described hereinabove may be constructed in different shapes (e.g. having oval, square etc. form in plan view) and sizes differing from those exemplified in the preceding description.

The above examples and description have been provided only for the purpose of illustration, and are not intended to limit the invention in any way. As will be appreciated by the skilled person, the invention can be carried out in a great variety of ways, employing more than one technique from those described above, all without exceeding the scope of the invention.

We claim:

1. A device for inducing in-vivo vibrations in a body passageway or an organ, comprising:
   a catheter tube;
   a series of magnets attached to the catheter tube, the magnets creating a magnetic field within at least one section of the catheter tube;
   a guidewire positioned in the catheter tube, the guidewire comprising a distal tip, followed by a flexible core member, followed by thicker core members, wherein the flexibility of the thicker core members is less than the flexibility of the flexible core member;
   the guidewire further comprising a plurality of electromagnet coils on at least one of the thicker core members, the coils creating an alternating magnetic field when activated with an alternating current by means of electrical leads;
   the alternating magnetic field of the coils being responsive to the magnetic field in the at least one section of the catheter tube to produce longitudinal oscillations in the guidewire when the coils overlap with the series of magnets.

2. A device according to claim 1, wherein each of the plurality of coils is capable of being independently fed with electrical current.

3. A device according to claim 1, wherein at least two of the plurality of coils are electrically connected to each other in a serial connection.

4. A device according to claim 1, wherein the plurality of coils are configured such that the directions of the electrical currents in adjacent pairs of coils are opposite.

5. A device according to claim 1, wherein the plurality of coils comprises at least one coil having multiple coil layers.

6. A device according to claim 1, wherein the plurality of coils comprises at least two coils that are spaced longitudinally from each other forming gaps along the guidewire, the guidewire further comprising at least one of passive coils and filling material that at least partially fill the gaps.

7. A device according to claim 6, wherein the filling material is at least one of a bio-compatible material and a thermally conductive material.

8. A device according to claim 1, wherein the plurality of coils comprises a coating, wherein the coating is one of a hydrophilic coating and a polytetrafluoroethylene (PTFE) based coating.

9. A device according to claim 1, wherein the electrical leads are attached along the guidewire by an electrically insulating shrinkable sleeve.

10. A device according to claim 1, wherein the guidewire further comprises an overall coil cover covering all of the core members, the coils being formed from sections of the overall coil cover.

11. A device according to claim 10, wherein the overall coil cover has a generally uniform stiffness along its length, the stiffness of the core members determines the stiffness of the guidewire.

12. A device according to claim 1, wherein the thickness of the core is tapered between adjacent core members.

13. A device according to claim 1, wherein the magnets are hollow shaped cylinders, the hollow shaped cylinders are spaced along the catheter tube, gaps being formed between adjacent hollow shaped cylinders.

14. A device according to claim 13, wherein each magnet has a north pole and a south pole on opposite faces of the cylinder, the south poles of adjacent magnets pointing in opposite directions.

15. A device according to claim 13, wherein the magnets are made of NdFeB rare earth material.

\* \* \* \* \*